(12) United States Patent
Leysieffer et al.

(10) Patent No.: US 7,376,563 B2
(45) Date of Patent: May 20, 2008

(54) SYSTEM FOR REHABILITATION OF A HEARING DISORDER

(75) Inventors: Hans Leysieffer, Taufkirchen (DE); Bernd Waldmann, München (DE)

(73) Assignee: Cochlear Limited, Lane Cove, NSW (AU)

(*) Notice: Subject to any disclaimer, the term of this patent is extended or adjusted under 35 U.S.C. 154(b) by 209 days.

(21) Appl. No.: 09/896,836

(22) Filed: Jul. 2, 2001

(65) Prior Publication Data
US 2002/0012438 A1 Jan. 31, 2002

(51) Int. Cl.
G10L 21/00 (2006.01)
G10L 11/00 (2006.01)
H04R 25/00 (2006.01)

(52) U.S. Cl. ............... 704/271; 704/206; 704/268; 381/312

(58) Field of Classification Search ............ 710/8; 704/268, 254, 259, 226, 207; 600/559; 381/60, 58, 317, 315, 314, 312; 379/338; 367/197
See application file for complete search history.

(56) References Cited

U.S. PATENT DOCUMENTS

| | | | |
|---|---|---|---|
| 3,557,775 A | 1/1971 | Mahoney | |
| 3,712,962 A | 1/1973 | Epley | |
| 3,764,748 A | 10/1973 | Branch et al. | |
| 4,352,960 A | 10/1982 | Dormer et al. | |
| 4,441,202 A | 4/1984 | Tong et al. | |
| 4,441,210 A | 4/1984 | Hochmair et al. | |
| 4,813,076 A | 3/1989 | Miller | |
| 4,820,059 A | 4/1989 | Miller et al. | |
| 4,988,333 A | 1/1991 | Engebretson et al. | |
| 5,015,224 A | 5/1991 | Maniglia | |
| 5,015,225 A | 5/1991 | Hough et al. | |
| 5,070,535 A | 12/1991 | Hochmair et al. | |
| 5,095,904 A | 3/1992 | Seligman et al. | |
| 5,113,859 A | 5/1992 | Funke | |
| 5,271,397 A | 12/1993 | Seligman et al. | |
| 5,279,292 A | 1/1994 | Baumann et al. | |
| 5,305,420 A | 4/1994 | Nakamura et al. | |

(Continued)

FOREIGN PATENT DOCUMENTS

DE 296 16 956 2/1997

(Continued)

OTHER PUBLICATIONS

Markowitz "Using Speech Recognition" 1996, Prentice Hall, pp. 44-47.*

(Continued)

*Primary Examiner*—V. Paul Harper
(74) *Attorney, Agent, or Firm*—Connolly Bove Lodge & Hutz, LLP

(57) ABSTRACT

A system for rehabilitation of a hearing disorder which comprises at least one acoustic sensor for picking up an acoustic signal and converting it into an electrical audio signal, an electronic signal processing unit for audio signal processing and amplification, an electrical power supply unit which supplies individual components of the system with current, and an actuator arrangement which is provided with one or more electroacoustic, electromechanical or purely electrical output-side actuators or any combination of these actuators for stimulation of damaged hearing, wherein the signal processing unit has a speech analysis and recognition module and a speech synthesis module.

49 Claims, 28 Drawing Sheets

U.S. PATENT DOCUMENTS

| | | | |
|---|---|---|---|
| 5,360,388 A | 11/1994 | Spindel et al. | |
| 5,411,467 A | 5/1995 | Hortman et al. | |
| 5,483,617 A | 1/1996 | Patterson et al. | |
| 5,545,219 A | 8/1996 | Kuzma | |
| 5,578,084 A | 11/1996 | Kuzma et al. | |
| 5,597,380 A | 1/1997 | McDermott et al. | |
| 5,601,617 A | 2/1997 | Loeb et al. | |
| 5,603,726 A | 2/1997 | Schulman et al. | |
| 5,604,812 A * | 2/1997 | Meyer | 381/314 |
| 5,608,803 A * | 3/1997 | Magotra et al. | 381/314 |
| 5,624,376 A | 4/1997 | Ball et al. | |
| 5,626,629 A | 5/1997 | Faltys et al. | |
| 5,749,065 A | 5/1998 | Nishiguchi et al. | |
| 5,772,575 A | 6/1998 | Lesinski et al. | |
| 5,774,857 A | 6/1998 | Newlin | |
| 5,795,287 A | 8/1998 | Ball et al. | |
| 5,800,475 A | 9/1998 | Jules | |
| 5,814,095 A | 9/1998 | Muller et al. | |
| 5,884,260 A * | 3/1999 | Leonhard | 704/254 |
| 5,909,497 A * | 6/1999 | Alexandrescu | 381/312 |
| 5,933,805 A * | 8/1999 | Boss et al. | 704/249 |
| 5,941,814 A | 8/1999 | Lehner et al. | |
| 5,951,601 A | 9/1999 | Lesinski | |
| 5,957,958 A | 9/1999 | Schulman et al. | |
| 5,977,689 A | 11/1999 | Neukermans | |
| 5,984,859 A | 11/1999 | Lesinski | |
| 5,997,466 A | 12/1999 | Adams et al. | |
| 5,999,632 A | 12/1999 | Leysieffer et al. | |
| 6,005,955 A | 12/1999 | Kroll et al. | |
| 6,029,131 A | 2/2000 | Bruckert | |
| 6,038,484 A | 3/2000 | Kuzma | |
| 6,047,074 A * | 4/2000 | Zoels et al. | 381/313 |
| 6,115,478 A * | 9/2000 | Schneider | 381/314 |
| 6,123,660 A | 9/2000 | Leysieffer | |
| 6,131,581 A | 10/2000 | Leysieffer et al. | |
| 6,198,971 B1 | 3/2001 | Leysieffer | |
| 6,227,204 B1 | 5/2001 | Baumann et al. | |
| 6,231,604 B1 * | 5/2001 | von Ilberg | 623/10 |
| 6,251,062 B1 | 6/2001 | Leysieffer | |
| 6,259,951 B1 * | 7/2001 | Kuzma et al. | 607/57 |
| 6,408,273 B1 | 6/2002 | Quagliaro et al. | |

FOREIGN PATENT DOCUMENTS

| | | |
|---|---|---|
| DE | 197 50 439 | 5/1998 |
| DE | 197 50 439 A1 | 6/1998 |
| DE | 197 22 705 A1 | 7/1998 |
| EP | 0 190 836 | 8/1986 |
| EP | 0 200 321 | 11/1986 |
| EP | 0 263 254 | 4/1988 |
| EP | 0 400 630 | 12/1990 |
| EP | 0 499 940 | 8/1992 |
| EP | 0548580 A1 * | 11/1992 |
| EP | 0 537 385 | 4/1993 |
| EP | 0 624 865 A1 | 11/1994 |
| EP | 0 831 673 | 3/1998 |
| EP | 0 831 674 | 3/1998 |
| EP | 0 984 663 | 3/2000 |
| EP | 0 984 664 | 3/2000 |
| EP | 1 006 511 A1 | 6/2000 |
| EP | 1 014 755 A2 | 6/2000 |
| EP | 1 083 769 A1 | 3/2001 |
| WO | WO 90/07251 | 6/1990 |
| WO | WO 96/06586 | 3/1996 |
| WO | WO 96/34508 | 10/1996 |
| WO | WO 99/03146 | 1/1999 |
| WO | WO 99/59134 | 11/1999 |

OTHER PUBLICATIONS

Sonntag et al. "Prosody Generation with a Neural Network: Weighing the Importance of Input Parameters" ICASSP 97, Muchnen, vol. 2, pp. 931-934.*

Fink, "Time-Reversed Acoustics", pp. 67-73, Nov. 1999, Scientific American 281:5.

Knor, "Tinnitus Retraining-Therapy and Hearing Acoustics", pp. 26 & 27, Feb. 1997.

Lehnhardt, "Intracochlear Placement of Cochlear Implant Electrodes in Soft Surgery Technique", pp. 356-359, 1993, HNO 41.

LePage et al., "Nonlinear Mechanical Behavior of the Basilar Membrane in the Basal Turn of the Guinea Pig Cochlea", pp. 183-189, 1980, Hearing Research 2.

Leysieffer et al., "A Totally Implantable-Hearing Device for the Treatment of Sensorineural Hearing Loss:TICA LZ 3001", pp. 853-863, 1998, HNO, vol. 46.

Mankin, "Machine Demonstrates Superhuman Speech Recognition Abilities", 3 pages, Sep. 30, 1999, USC News Service, Release No. 0999025.

Muller-Deile et al., "Cochlear Implant Supply for Non-Deaf Patients", pp. 136-143, 1998, Laryngo-Rhino-Otol. 77.

Ruh et al., "Cochlear Implant for Patients with Residual Hearing", pp. 347-350, 1997, Laryngo-Rhino-Otol. 76.

Suzuki et al., "Implantation of Partially Implantable Middle Ear Implant and the Indication", pp. 160-166, Karger Basel 1988, Advances in Audiology, vol. 4.

Yanagihara et al., "Implantable Hearing Aid", pp. 160-166, Karger Basel 1988, Arch Otolaryngol Head Neck, Surg-vol. 113.

Zenner et al., "Horen (Physiologie, Biochemie, Zell-and Neurobiologie", pp. 20-23 and 107 & 108, 1994, Georg Thieme Verlag Stuttgart-New York.

Zenner et al., "First Implantations of a Totally Implantable Electronic Hearing System for a Sensorineural Hearing Loss", pp. 844-852, 1998, HNO vol. 46.

Zenner et al., "Active Electronic Hearing Implants for Patients with Conductive and Sensorineural Hearing Loss-a New Era of Ear Surgery", pp. 749-774, 1997, HNO vol. 45.

Zenner, "Totally Implantable Hearing Device for Sensorineural Hearing Loss", p. 1751, Nov. 28, 1998, The Lancet, vol. 352, No. 9142.

Zadak, et al., "*An Application of Mapping Neural Networks and a Digital Signal Processor for Cochlear Neuroprostheses*", Biological Cybernetics, vol. 68, pp. 545-552, Apr. 1, 1993.

European Search Report dated Nov. 26, 2003.

Leisenberg, M.; Hearing Aids for the Profoundly Deaf Based on Neural Net Speech Processing; Acoustics, Speech, and Signal Processing, 1995; ICASSP-95; 1995 International Conference on Detroit, MI; USA May 9-12, 1995, New York, NY, USA, IEEE, US, BD. 5, May 9, 1995; pp. 3535-3538, XP010152110; ISBN: 0-7803-2431-5; The Whole Document.

* cited by examiner

SYSTEM FOR REHABILITATION OF A HEARING DISORDER

BACKGROUND OF THE INVENTION

1. Field of the Invention

This invention relates to a system for rehabilitation of a hearing disorder which comprises at least one sensor which picks up sound, an electronic signal processing unit for audio signal processing and amplification, an electrical power supply unit which supplies individual components of the system with current, and one or more electroacoustic, electromechanical or purely electrical output-side actuators or any combination of these actuators for stimulation of damaged hearing.

2. Description of the Related Art

Hearing systems are defined here as systems in which the acoustic signal is picked up with at least one sensor which converts the acoustic signal into an electrical signal (microphone function), which is electronically further processed and amplified, and whose output-side signal stimulates the damaged hearing acoustically, mechanically or electrically or by some combination of these three forms of physical stimulation.

The expression "hearing disorder" is defined here as all types of inner ear or retro-cochlear damage, combined inner ear and middle ear damage, and also temporary or permanent noise impression (tinnitus).

Conventional hearing aids with output-side acoustic stimulation of damaged hearing, especially of the inner ear, in recent years have undergone major improvements with respect to electronic signal processing which are based especially on use of modern fully digital signal processors. Using these processors and the corresponding signal processing software, the rehabilitation of a hearing disorder can be optimized by refined matching to the individual hearing damage. In particular, for the first time, noise or interfering signal-suppressing algorithms can be implemented which especially take into account the circumstance that mainly those with sensorineural hearing damage have major problems in understanding of speech of individuals when they are in a noisy environment.

In recent years rehabilitation of sensorineural hearing disorders with partially implantable electronic systems has acquired major importance. In particular, this applies to the group of patients in which hearing has completely failed due to accident, illness or other effects or in which hearing is congenitally non-functional. If, in these cases, only the inner ear (cochlea), and not the neural auditory path which leads to the brain, is affected, the remaining auditory nerve can be stimulated with electrical stimulation signals. Thus, a hearing impression can be produced which can lead to speech comprehension. In these so-called cochlear implants (CI), an array of stimulation electrodes, which is controlled by an electronic system (electronic module) is inserted into the cochlea. This electronic module is encapsulated with a hermetical, biocompatible seal and is surgically embedded in the bony area behind the ear (mastoid). The electronic system contains essentially only decoder and driver circuits for the stimulation electrodes. Acoustic sound reception, conversion of this acoustic signal into electrical signals and their further processing, always takes place externally in a so-called speech processor which is worn outside on the body. The speech processor converts the preprocessed signals into a high frequency carrier signal which, via inductive coupling, is transmitted through the closed skin (transcutaneously) to the implant. The sound-receiving microphone is always located outside of the body, and in most applications, in a housing of a behind-the-ear hearing aid worn on the external ear. The microphone is connected to the speech processor by a cable. Such cochlear implant systems, their components, and the principles of transcutaneous signal transmission are described, by way of example, in published European Patent Application EP 0 200 321 A2 and in U.S. Pat. Nos. 5,070,535, 4,441,210, 5,626,629, 5,545,219, 5,578,084, 5,800,475, 5,957,958 and 6,038,484. Processes of speech processing and coding in cochlear implants are described, for example, in published European Patent Application EP 0 823 188 A1, in European Patent 0 190 836 A1 and in U.S. Pat. Nos. 5,597,380, 5,271,397, 5,095,904, 5,601,617 and 5,603,726.

In addition to rehabilitation of congenitally deaf persons and those who have lost their hearing using cochlear implants, for some time, there have been approaches to offer better rehabilitation than with conventional hearing aids to patients with a sensorineural hearing disorder which cannot be surgically corrected by using partially or totally implantable hearing aids. The principle arises, in most embodiments, in stimulating an ossicle of the middle ear or directly stimulating the inner ear via mechanical or hydromechanical means, and not via the amplified acoustic signal of a conventional hearing aid in which the amplified acoustic signal is supplied to the external auditory canal. The actuator stimulus of these electromechanical systems is accomplished with different physical transducer principles, such as, for example, by electromagnetic and piezoelectric systems. The advantage of these devices is seen mainly in the sound quality which is improved as compared to conventional hearing aids, and for totally implanted systems, in the fact that the hearing prosthesis is not visible.

Such partially and fully implantable electromechanical hearing aids are described, for example, by Yanigahara et al. "Implantable Hearing Aid", Arch Otolaryngol Head Neck Surg-Vol 113, 1987, pp. 869-872; Suzuki et al. "Implantation of Partially Implantable Middle Ear Implant and the Indication", Advances in Audiology, Vol. 4, 160-166, Karger Basel, 1988; H. P. Zenner et al. "First implantations of a totally implantable electronic hearing system for sensorineural hearing loss", in HNO Vol. 46, 1998, pp. 844-852; H. Leysieffer et al. "A totally implantable hearing device for the treatment of sensorineural hearing loss: TICA LZ 3001", HNO Vol. 46, 1998, pp. 853-863; H. P. Zenner et al. "Active electronic hearing implants for patients with conductive and sensorineural hearing loss—a new era of ear surgery", HNO 45: 749-774; H. P. Zenner et al. "Totally implantable hearing device for sensorineural hearing loss", The Lancet Vol. 352, No. 9142, page 1751; and are described in numerous patent documents among others in published European Patent Applications EP 0 263 254 A1, EP 0 400 630 A1, and EP 0 499 940 A1, and in U.S. Pat. Nos. 3,557,775, 3,712,962, 3,764,748, 5,411,467, 4,352,960, 4,988,333, 5,015,224, 5,015,225, 5,360,388, 5,772,575, 5,814,095, 5,951,601, 5,977,689 and 5,984,859. Here, the insertion of an electromechanical transducer through an opening in the promontory for direct fluid stimulation in the inner ear is described in U.S. Pat. Nos. 5,772,575, 5,951,601, 5,977,689 and 5,984,859.

Recently, partially and fully implantable hearing systems for rehabilitation of inner ear damage have been in clinical use. Depending on the physical principle of the output-side electromechanical converter, and especially its coupling type to the ossicle of the middle ear, it happens that the attained results of improving speech understanding can be very different. In addition, for many patients, a sufficient loudness level cannot be reached. This aspect is spectrally very diverse; this can mean that, at medium and high frequencies, for example, the generated loudness is sufficient, but not at low frequencies, or vice versa.

Furthermore the spectral bandwidth which can be transmitted can be limited, thus, for example, to low and medium frequencies for electromagnetic converters and to medium and high frequencies for piezoelectric converters. In addition, nonlinear distortions, which are especially pronounced in electromagnetic converters, can have an adverse effect on the resulting sound quality. The lack of loudness leads especially to the fact that the audiological indication range for implantation of an electromechanical hearing system is very limited. This means that patients, for example, with sensorineural hearing loss of greater than 50 dB HL (hearing loss) in the low tone range can only be inadequately supplied with a piezoelectric system. Conversely, pronounced high tone losses can only be poorly supplied with electromagnetic converters.

Many patients with inner ear damage also suffer from temporary or permanent noise impressions (tinnitus) which cannot be surgically corrected and for which, to date, there are no approved drug treatments. Therefore, so-called tinnitus maskers (International Patent Application Publication WO-A 90/07251, published European Patent Application EP 0 537 385 A1, German Utility Model No. 296 16 956) are known. These devices are small, battery-driven devices which are worn like a hearing aid behind or in the ear and which, by means of artificial sounds which are emitted into the auditory canal, for example, via a hearing aid speaker, psychoacoustically mask the tinnitus, and thus, reduce the disturbing noise impression, if possible, to below the threshold of perception. The artificial sounds are often narrowband noise (for example, third-band noise). The spectral position and the loudness level of the noise can be adjusted via a programming device to enable adaptation to the individual tinnitus situation as optimally as possible. In addition, the so-called retraining method has been developed recently in which, by combination of a mental training program and presentation of broadband sound (noise) near the auditory threshold, the perceptibility of the tinnitus in quiet conditions is likewise supposed to be largely suppressed (H. Knoer "Tinnitus retraining therapy and hearing acoustics" journal "Hoerakustik" February 1997, pages 26 and 27). These devices are also called "noisers".

In the two aforementioned methods for hardware treatment of tinnitus, hearing aid-like, technical devices must be carried visibly outside on the body in the area of the ear; these devices stigmatize the wearer and, therefore, are not willingly worn.

U.S. Pat. No. 5,795,287 describes an implantable tinnitus masker with direct drive of the middle ear, for example, via an electromechanical transducer coupled to the ossicular chain. This directly coupled transducer can preferably be a so-called "Floating Mass Transducer" (FMT). This FMT corresponds to the transducer for implantable hearing aids which is described in U.S. Pat. No. 5,624,376.

In commonly owned, co-pending U.S. patent application Ser. Nos. 09/372,172 and 09/468,860, which are hereby incorporated by reference, implantable systems for treatment of tinnitus by masking and/or noiser functions are described, in which the signal-processing electronic path of a partially or totally implantable hearing system is supplemented by corresponding electronic modules, such that the signals necessary for tinnitus masking or noiser functions can be fed into the signal processing path of the hearing aid function and the pertinent signal parameters can be individually adapted by further electronic measures to the pathological requirements. This adaptability can be accomplished by storing or programming the necessary setting data of the signal generation and feed electronics by using hardware and software in the same physical and logic data storage area of the implant system, and by controlling the feed of the masker or noiser signal into the audio path of the hearing implant via the corresponding electronic actuators.

The above described at least partially implantable hearing systems for rehabilitation of inner ear damage, which are based on an output-side electromechanical transducer, differ from conventional hearing aids essentially only in that the output-side acoustic stimulus (i.e., an amplified acoustic signal in front of the eardrum) is replaced by an amplified mechanical stimulus of the middle ear or inner ear. The acoustic stimulus of a conventional hearing aid ultimately leads to vibratory, i.e., mechanical, stimulation of the inner ear, via mechanical stimulation of the eardrum and the subsequent middle ear. The requirements for effective audio signal preprocessing are fundamentally similar or the same. Furthermore, in both embodiments on the output side a localized vibratory stimulus is ultimately routed to the damaged inner ear (for example, an amplified mechanical vibration of the stapes in the oval window of the inner ear).

Basically, in this routinely used rehabilitation of inner ear damage by active hearing systems (regardless of whether the rehabilitation is by an external acoustic stimulus or by an implanted electromechanical stimulus), at present, there is a major drawback which is described below in summary for understanding of this invention: most cases of sensorineural deafness are based on more or less pronounced damage of the outer hair cells in the inner ear. These outer hair cells, which in large number are located in the organ of Corti along the basilar membrane, form part of the so-called cochlear amplifier which, depending on local excitation of the basilar membrane as a result of traveling wave formation, actively mechanically de-attenuate this local stimulation range at low levels, and thus, small traveling wave amplitudes, which leads to an increase in sensitivity. This active amplification is based on a very complex, efferently controlled process which is not described here. Furthermore, it is assumed that, at very high levels of inner ear stimulation as a result of the high loudness, this effect is reversed in its action, and thus, locally reduces and actively attenuates the traveling wave amplitude. These nonlinear characteristics of the cochlear amplifier, which is located along the organ or Corti in several hundred functional units with locally limited action, are of decisive importance for the function of the healthy inner ear. In partial or total failure of the outer hair cells, in addition to a loss of sensitivity, which leads to a rise in the hearing threshold, other disadvantages arise: the described active de-attenuation of the basilar membrane leads to high Q-factors of the envelopes of the traveling waves (tuning curves) which are essentially responsible for the frequency differentiation capacity (tone pitch differences). If this high quality is lacking due to failure or partial damage of the outer hair cells, the affected individual can perceive tone pitch differences much more poorly. The rise of the hearing threshold leads, moreover, to a reduction of the dynamic range since the upper sensory boundary (discomfort threshold) in labyrinthine deafness does not rise at the same time. This reduction of dynamics results in an increased perception of loudness which is called positive recruitment. The described effects, which are caused by damage or failure of the outer hair cells, lead, in the overall effect for the affected individual, to a reduction in speech comprehension, especially in a noisy environment (summary description in Zenner, H. P.: *Hearing*, Georg Thieme Verlag Stuttgart, New York, 1994, pages 20-23, 107 and 108, and LePage, E. W., Johnstone, M. B.: "Non-linear mechanical behavior of the basilar membrane in the basal turn of the guinea pig cochlea." Hearing Research 2 (1980), pp. 183-189).

An important consequence of this described mechanism is that, as indicated above, both in conventional acoustic hearing aids and also in partially or fully implantable hearing systems, the important functions of the damaged outer hair cells, and thus, of the cochlear amplifier, cannot be replaced or at least partially restored. U.S. Pat. No. 6,123, 660 discloses a converter arrangement for partially or fully implantable hearing aids for direct mechanical excitation of the middle ear or inner ear, which is provided with a piezoelectric converter element and also with an electromagnetic converter which are accommodated in a common housing and the two can be coupled via the same coupling element to the middle ear ossicle or directly to the inner ear. Furthermore, implantable hearing systems are known (U.S. Pat. Nos. 5,997,466 and 6,005,955) which work with two or more output-side electromechanical converters in one or locally separate arrangements. These embodiments are, however, uniquely described in that a system design with more than one converter enables a linear superposition of the deflection frequency responses of the individual converters which, as a result, allows an output-side excitation form of the cochlea which is adjustable or programmable depending specifically on frequency or spectrally optimized as much as possible and thus will lead to a spectrally balanced and sufficient loudness impression of the implant system. Rehabilitation of the cochlear amplifier with the aforementioned features is, however, not possible by these embodiments or described signal preprocessing methods.

In cochlear implants (CI), solely electrical stimulation signals are now used as the actuator stimuli. After implantation of a CI in completely deaf patients, training is generally necessary for rehabilitation of hearing, since the artificial stimuli must be learned, because the artificial stimuli do not fundamentally correspond to thee biologically proper form of stimulation of the inner ear. Conversely, this rehabilitation phase is omitted after implantation of an electromechanical hearing system in those with hearing difficulties since the mechanical form of stimulation is biologically suitable, as described above, and since the mechanical form of stimulation ultimately largely corresponds with a hearing aid at least with respect to the basic function, i.e., the stimulation at the input of the inner ear is of a vibratory nature.

Recently, it has become scientifically known from CI implantations that even for incomplete deafness cochlear implants (CIs) can be successfully used when sufficient speech discrimination can no longer be achieved with a conventional hearing aid. Interestingly, it was demonstrated that the important inner ear structures which enable residual acoustic hearing capacity can be maintained in part or largely stably over time when a CI electrode is inserted into the cochlea (S. Ruh et al.: "Cochlear implant for patients with residual hearing", Laryngo-Rhino-Otol. 76 (1997) pp. 347-350; J. Mueller-Deile et al.: "Cochlear implant supply for non-deaf patients?" Laryngo-Rhino-Otol. 77 (1998) pp. 136-143; E. Lehnhardt: "Intracochlear placement of cochlear implant electrodes in soft surgery technique", HNO 41 (1993), pp. 356-359). In the foreseeable future, it certainly will be possible, in case of residual hearing capacity, to clinically place CI electrodes intracochlearly in a manner such that the remaining inner ear structures can be preserved over the long term, and thus, can continue to be stimulated in a biologically proper manner, i.e., vibrationally, and lead to a usable hearing impression.

Therefore, the recent patent literature contains new approaches to "replacing" the damaged cochlear amplifier by a multichannel intracochlear converter array with a purely mechanical or mixed mechanical/electrical form of stimulation (commonly owned co-pending U.S. patent application Ser. Nos. 09/833,704, 09/833,642, 09/833,643). Whether these solutions will lead to a clear improvement of speech understanding especially in a noisy environment however cannot yet be foreseen.

Therefore, in all the described processes in currently available systems, there remains the serious defect that especially speech understanding in a noisy environment is greatly reduced. This applies especially in cochlear implants in which, due to a physiologically improper form of electrical stimulation, the patients must more or less learn a new language, the understanding or interpretation of which is of course more prone to interfering signal portions.

Especially in fully implantable hearing systems can this defect be reduced by an optimized microphone position near the eardrum (see published European Patent Applications EP 0 831 673 A2, EP 0 831 674 A1 and U.S. Pat. No. 5,814,095) since, in this way, the natural directional action of the outer ear is used. These directional effects are approached in conventional hearing aids by the suitable wiring of several, locally separate microphones. But these measures are relatively ineffectual when the useful and interfering sound comes from the same direction.

This serious defect can be reduced only to a certain extent by modern digital speech process algorithms with interfering signal reduction. For example, the input signal is divided into several frequency bands. In each band, using simple signal-statistical criteria (for example modulation parameters) it is evaluated whether it is a speech or an interference signal in this band. Bands in which the algorithm detects speech signals are raised in their amplification, conversely bands in which mainly interfering sound predominates are attenuated. It is important here that this process which is frequently used today cannot change the signal-noise ratio in a band and thus cannot improve it. It is common to all the analysis processes used that they use only elementary signal-statistical parameters (for example, amplitude modulation depth and frequency).

Further, it is common to all the described rehabilitation processes that they do analyze, process and amplify the audio signal or speech signal, and in cochlear implants, code it into a new form of stimulation. Transmission of direct speech information in more or less real time is however preserved. This results in that interfering signal portions can also be approximately recognized by analysis processes and reduced. Genuine separation of speech and noise information however does not occur.

SUMMARY OF THE INVENTION

A primary object of the present invention is to devise a system for rehabilitation of a hearing disorder which is able to offer speech from which interfering noise has been at least largely removed at the output of the system.

This object is achieved in that, in a system for rehabilitation of a hearing disorder which comprises at least one acoustic sensor (microphone) for picking up an acoustic signal and converting it into an electrical audio signal, an electronic signal processing unit for audio signal processing and amplification, an electrical power supply unit which supplies individual components of the system with current, and an actuator arrangement which is provided with one or more electroacoustic, electromechanical or purely electrical output-side actuators or any combination of these actuators for stimulation of the damaged hearing, according to the invention, the signal processing unit has a speech analysis and recognition module and a speech synthesis module which execute speech analysis and subsequent speech synthesis.

With the system in accordance with the invention, speech analysis and speech recognition and speech synthesis are carried out to improve the transmission of speech information especially in a noisy environment. Thus, the aforementioned defects are essentially circumvented. An electronic signal processing system undertakes genuine speech information analysis (speech information segmentation or recognition). Based on the resulting information a speech output is produced which is based on genuine synthesis. Thus, a purely artificially produced, synthesized speech signal is output which is essentially without any input-side interference signal portions. At least approximately, the interference signals are completely removed; among others, this leads to a major improvement of the transmission of speech information in a noisy environment. Another advantage of this approach is that especially in hearing systems with acoustic and/or mechanical output-side stimulation of hearing, feedback to the sound-receiving sensor or the microphone is largely avoided or completely eliminated.

The signal processing unit preferably has a digital signal processor which contains software modules for speech analysis and synthesis. These modules are advantageously built to be adaptive, and if necessary, can be reprogrammed, especially to enable optimization of speech analysis and synthesis.

Preferably, to analyze the input signal, there is a digitally implemented neural network which operates with automatic algorithms and which, in the course of analysis, assigns the input signal to phonetic or lexical categories. This phonetic or lexical information represents the input signals for a subordinate speech synthesis module with an output signal which is thus transmitted to the damaged hearing roughly noise-free by acoustic, mechanical, electrical or optionally combinatorial means. Here, to prevent an especially monotone impression of the re-synthesized speech, it can be a very good idea to provide an arrangement which extracts information about the emotional state of the speaker or his intention in, for example, question formulations or requests and transmits it, at the same time, i.e., in this case, suitably synthesized. This additional information is generally called the prosody of the speech. Detection of these prosodic features can comprise, for example, in extraction of the level and the characteristic of fundamental speech frequencies in voiced sounds, such as vowels. On the synthesis side of the system, the output signal is modulated accordingly in order to transmit this information.

Furthermore, it can be a good idea to temporarily turn off the analysis and synthesis system and to transmit the speech signal or the audio signal like, for example, music in the conventional manner, if there is little or no interfering sound. This function can take place automatically or by a remote control function by the user.

Basic processes of speech analysis, recognition and synthesis which can be used in this invention are described in International Patent Application Publication WO 99/59134 and U.S. Pat. Nos. 5,483,617, 4,820,059, 4,813,076, 5,749, 065, 5,305,420, 6,029,131 and especially by Eric Mankin: "Machine demonstrates superhuman speech recognition abilities" in USC News Service, Release number: 0999025, Release date: Sep. 30, 1999.

In another embodiment of the invention, the signal processing unit can contain software modules which enables masking of tinnitus parallel to operation of the hearing aid. Especially in the case of multichannel hearing systems, can a tinnitus which can be at least peripherally localized be masked more effectively than with conventional tinnitus maskers.

The signal processing unit feasibly has a preprocessing arrangement for pre-amplification and/or filtering and for analog-digital (A/D) conversion of the acoustic sensor signals. It can in particular comprise anti-aliasing filters. In the presence of several acoustic sensors and/or several output-side actuators, feasibly each acoustic sensor is upstream of its own analog-digital converter and each output-side actuator is downstream of its own digital-analog converter.

The signal processing unit advantageously has a digital signal processor for processing the A/D-converted acoustic sensor signals which have been optionally preprocessed by means of the preprocessing arrangement and/or for generation of digital signals for tinnitus masking.

This hearing system can be made non-implantable. However, it is preferable if it is made at least partially implantable, then a preferably PC-based, wireless telemetry means can be provided for transmission of data between the implanted part of the system and an external unit, especially an external programming system.

The existing software modules of the hearing system can be designed to be static such that, as a result of scientific findings, they are filed once in the program storage of the digital signal processor and remain unchanged. But then, if later, for example, due to more recent scientific findings, improved algorithms for speech signal conditioning and processing are available and they are to be used, in an implanted system, the entire implant or implant module which contains the corresponding signal processing unit must be replaced by a new unit with the altered operating software by invasive surgery on the patient. This surgery entails renewed medical risks for the patient and is very complex.

This problem can be solved in another embodiment of the invention by an at least partially implantable hearing system being provided with the aforementioned telemetry means a rewritable implantable storage arrangement which is assigned to the signal processor for accommodating and reproducing the operating program, and at least parts of the operating program can be replaced or changed by data transmitted from the external unit via the telemetry means. In this way, after implantation of the implantable system, the operating software can be changed or even completely replaced, as is explained for otherwise known systems for rehabilitation of hearing disorders in commonly owned U.S. Pat. No. 6,198,971 which is hereby incorporated by reference.

Preferably, the design is such that, in addition, for fully implantable systems, in the known manner, the operating parameters, i.e., the patient-specific data, for example, audiological adaption data, or variable implant system parameters (for example, as a variable in a software program for control of battery recharging) can be transmitted transcutaneously into the implant after implantation, i.e., wirelessly through the closed skin, and thus, can be changed. Here, preferably, not only the speech analysis and recognition module and the speech synthesis module, but also other software modules implemented in the signal processing unit and/or in the power supply unit are designed to be preferably dynamic (adaptive) or re-programmable. In particular, the software modules can be designed to be adaptive, and parameter matching can be done by training by the implant wearer and using other aids.

This approach allows matching of the system to circumstances which can be detected only after implantation of the implantable system. Thus, for example, in an at least partially implantable hearing system for rehabilitation of a monaural or binaural inner ear disorder and of a tinnitus by mechanical stimulation of the inner ear, the sensoric (acoustic sensor or microphone) and actoric (output stimulator) biological interfaces are always dependent on anatomic, biological and neurophysiological circumstances, for example, on the inter-individual healing process. These interface parameters can also be individual, also especially time-variant. Thus, for example, the transmission behavior of an implanted microphone can vary inter-individually and individually as a result of being covered by tissue, and the transmission behavior of an electromechanical transducer which is coupled to the inner ear can vary in view of on different coupling qualities. These differences of interface parameters which cannot be eliminated or reduced in the devices known from the prior art, even by replacing the implant, can now be optimized by changing or improving the signal processing of the implant.

In an at least partially implantable hearing system, it can be advisable or become necessary to implement signal processing algorithms which have been improved after implantation. Especially the following should be mentioned here:

speech analysis processes (for example, optimization of a fast Fourier transform (FFT))
static or adaptive noise detection processes
static or adaptive noise suppression processes
processes for optimization of the signal to noise ratio within the system
optimized signal processing strategies in progressive hearing disorder
output level-limiting processes for protection of the patient in case of implant malfunctions or external faulty programming
processes of preprocessing of several sensor (microphone) signals, especially for binaural positioning of the sensors
processes for binaural processing of two or more sensor signals in binaural sensor positioning, for example optimization of spacial hearing or spacial orientation
phase or group delay time optimization in binaural signal processing processes for optimized driving of the output stimulators, especially for binaural positioning of the stimulators.

Among others, the following signal processing algorithms can be implemented with this system even after implantation:

processes for feedback suppression or reduction
processes for optimization of the operating behavior of the output transducer(s) (for example, optimization of the frequency response and phase response, improvement of the impulse response)
speech signal compression processes for sensorineural hearing loss
signal processing methods for recruitment compensation in sensorineural hearing loss.

Furthermore, in implant systems with a secondary power supply unit, i.e., a rechargeable battery system, but also in systems with primary battery supply, it can be assumed that these electrical power storages will enable longer and longer service lives and thus increasing residence times in the patients as technology advances. It can be assumed that fundamental and applied research for signal processing algorithms will make rapid progress. The necessity or the patent desire for operating software adaptation and modification will therefore presumably take place before the service life of the implanted power source expires. The system described here allows this adaptation of the operating programs of the implant even when the implant has already been implanted.

Preferably, a buffer storage arrangement is provided in which data transmitted from the external unit via the telemetry means can be buffered before being relayed to the signal processor. In this way, the transmission process from the external unit to the implanted system can be terminated before the data transmitted via the telemetry means are relayed to the signal processor.

Furthermore, a checking logic can be provided which checks the data stored in the buffer storage arrangement before relaying the data to the signal processor. There can be provided a microprocessor module, especially a microcontroller, for control of the A/D converters and/or the D/A converters and/or the signal processor within the implant via a data bus, the checking logic and the buffer storage arrangement preferably being implemented in the microprocessor module, and wherein also program parts or entire software modules can be transferred via the data bus and the telemetry means between the outside world, the microprocessor module and the signal processor.

An implantable storage arrangement for storing the working program for the microprocessor module is preferably assigned to the microprocessor module, and at least parts of the working program for the microprocessor module can be changed or replaced by data transmitted from the external unit via the telemetry means.

In another embodiment of the invention, at least two storage areas for storage and retrieval of at least the operating program of the signal processor may be provided. This contributes to the reliability of the system, in that due to the multiple presence of a storage area which contains the operating program(s), for example, after transmission from the exterior or when the implant is turned on, checking for the absence of faults in the software can be performed.

Analogously to the above, the buffer storage arrangement can also comprise at least two storage areas for storage and retrieval of data transferred from the external unit via the telemetry means, so that after data transmission from the external unit still in the area of the buffer storage the absence of errors in the transferred data can be checked. The storage areas can be designed, for example, for complementary filing of the data transferred from the external unit. However, at least one of the storage areas of the buffer storage arrangement can also be designed to store only part of the data transferred from the external unit, wherein the absence of errors in the transferred data is checked in sections, in this case.

Furthermore, to ensure that in case of transmission errors, a new transmission process can be started, a preprogrammed read-only memory area which cannot be overwritten can be assigned to the signal processor, in which ROM area the instructions and parameters necessary for "minimum operation" of the system are stored, for example, instructions which after a "system crash" ensure at least error-free operation of the telemetry means for receiving an operating program and instructions for its storage in the control logic.

As already mentioned, the telemetry means is advantageously designed not only for reception of operating programs from the external unit, but also for transfer of operating parameters between the implantable part of the system and the external unit such that, on the one hand, such parameters (for example, the volume) can be adjusted by a physician, a hearing aid acoustics specialist or the wearer of the system himself, and on the other hand the system can also transfer the parameters to the external unit, for example, to check the status of the system.

A totally implantable hearing system of the aforementioned type can have, in the implanted portion, in addition to the actoric stimulation arrangement and the signal processing unit, at least one implantable acoustic sensor and a rechargeable electrical storage element, and in this case, a wireless transcutaneous charging device can be provided for charging of the storage element. For a power supply, there can also be provided a primary cell or another power supply unit which does not require transcutaneous recharging. This applies especially when it is considered that, in the near future, mainly by continuing development of processor technology, a major reduction in power consumption for electronic signal processing can be expected so that, for implantable hearing systems, new forms of power supply will become usable in practice, for example, a power supply which uses the Seebeck effect, as is described in U.S. Pat. No. 6,131,581. Preferably, there is also provided a wireless remote control for control of the implant functions by the implant wearer.

In case of a partially implantable hearing system, at least one acoustic sensor, an electronic signal processing arrangement, a power supply unit and a modulator/transmitter unit are contained in an external module which can be worn outside on the body, especially on the head over the implant. The implant comprises the output-side electromechanical transducer and the intracochlear stimulation electrode array, but is passive in terms of energy and receives its operating energy and transducer control data via the modulator/transmitter unit in the external module.

In another embodiment of the invention, electromechanical converters for excitation of the fluid-filled inner-ear spaces of the damaged inner ear may be provided as the output-side actuators, and the signal processing unit can have driving signal processing electronics which electrically triggers each of the converters such that on the basilar membrane of the damaged inner ear a travelling wave configuration is formed which approximates the type of travelling wave formation of a healthy undamaged inner ear.

Preferably, the output-side electromechanical converters are designed for direct excitation of the fluid-filled inner ear spaces of the damaged inner ear. This direct stimulation of the cochlea prevents or largely reduces the occurrence of feedback, i.e., coupling of the output signal into the sensor (microphone), because the ossicle chain, and thus, the eardrum, are not excited to vibrations or at least are to a reduced degree. This is especially advantageous when an acoustic sensor (microphone function) is applied in the immediate vicinity of the eardrum, as is known from U.S. Pat. Nos. 5,814,095 and 5,999,632.

Direct excitation of the fluid-filled inner ear spaces of the damaged inner ear can be achieved by an intracochlear array of output-side actuators in the form of electromechanical converters. This converter array is implanted directly into the fluid-filled space of the inner ear (scala tympani or scala vestibuli).

The intracochlear converter array preferably has a total diameter in the range from 0.4 mm (apical area) to 2.0 mm (basal area) and a total length between 5 mm and 50 mm. It feasibly has a carrier of a biocompatible material which is biostable in the inner ear, preferably a polymer, especially a silicone. The individual output-side electromechanical converters can be embedded in the carrier for reasons of biocompatibility such that they are completely surrounded by a thin layer of the carrier material.

In order to minimize mechanical wave propagation from a converter within the carrier to adjacent converters, between the individual output-side electromechanical converters mechanical attenuation elements are embedded in the carrier, the material of the attenuation elements for a similar cross sectional geometry to that of the carrier being preferably chosen such that to achieve high attenuation values there is a high mechanical impedance difference compared to the carrier material.

However, according to one modified embodiment, there can be an extracochlear multichannel array of output actuators, in the form of electromechanical converters, which is fixed from the outside on the cochlea. This extracochlear converter array can be developed and produced, as a whole, simply and with high precision in processes conventional in semiconductor manufacture using microsystems engineering techniques, for example, photolithographically. These processes allow a high level of miniaturization and excellent reproducibility of the individual converters on an array. The properties of production by microsystems engineering are especially advantageous here because, in the intended function of the array, the phase synchronism of the individual converters on the array is very important. Details of microsystems engineering processes are described, among others, in International Patent Application Publication WO 99/03146 and do not require further explanation here.

For the extracochlear converter array there can advantageously be a substrate which contains an electrical termination panel which is produced at the same time using microsystems engineering and is designed for connection of a multipin, biocompatible implant line to a module which contains the driving signal processing electronics. The substrate of the extracochlear converter array can furthermore be provided with an electronic module which was produced at the same time using microsystems engineering and which can contain especially driver stages for triggering the output-side electromechanical converters and/or decoding logic and converter modules for connection of a pin-reduced implant line. Thus, the array terminal can consist of only three lines, especially one ground line, one data line and one clock signal line, and supply of electrical operating energy can take place by phantom feed on the clock signal line.

The electronic module can also contain an interface module for digital data transmission via the implant line, preferably by means of an optical fiber, and/or for serial data transmission on the implant feeder line D/A converters and driver modules assigned to the converters. Feasibly, the extracochlear converter array, including the carrier structure, (substrate) is equipped with biocompatible jacketing which preferably is formed of polymers known from implant technology, especially polytetrafluorethylene, polyurethane or silicones.

Direct excitation of the fluid-filled inner ear spaces, when using an extracochlear converter array, can be provided by the converters each having an output-side coupling element which is made such that it projects through an artificial access to the inner ear (openings or holes in the bony outer wall of the cochlea, so-called "cochleostomies").

The electronic module can also contain an interface module for digital data transmission via the implant line, preferably by means of an optical fiber, and/or for serial data transmission on the implant feeder line D/A converters and driver modules assigned to the converters.

Feasibly, the extracochlear converter array, including the carrier structure (substrate), is equipped with biocompatible jacketing, which preferably is made of polymers known from implant technology, especially polytetrafluorethylene, polyurethane or silicones.

Advantageously, the output-side electromechanical converters in the pertinent converter array are arranged distributed equidistantly or at logarithmic distances according to the tonotopic frequency-location assignment along the basilar membrane of the inner ear, and in the case of a tonotopic arrangement, a number of converters from 20 to 24 according to psychoacoustical frequency bands can lead to especially favorable results.

According to one modified embodiment of the invention, the actuator arrangement in combination has an electromechanical converter for mechanical stimulation of the middle ear or inner ear and an intracochlear, electrically acting stimulation electrode array with at least one stimulation electrode for electrical stimulation of the inner ear.

Furthermore, there can advantageously be a dual intracochlear arrangement as the actuator stimulation arrangement which, in combination, has a stimulator arrangement with at least one stimulator element for at least indirect mechanical stimulation of the inner ear and an electrically acting stimulation electrode array with at least one stimulation electrode with at least one cochlear implant electrode for electrical stimulation of the inner ear.

Recently, in partially and fully implantable hearing systems for rehabilitation of inner ear damage which have been in clinical use, in which there is an electromechanical actuator coupled to the ossicle chain, depending on the physical principle of the output-side electromechanical converter and especially its type of coupling to the ossicle of the middle ear, it happens that the attained results of improving speech understanding can be very different. In addition, for some patients a sufficient loudness level cannot be reached. This aspect is spectrally very diverse; this can mean that at medium and high frequencies for example, the generated loudness is sufficient, but not at low frequencies, or vice versa. Furthermore, the spectral bandwidth which can be transmitted can be limited, thus for example, to low and medium frequencies for electromagnetic converters and to medium and high frequencies for piezoelectric converters. In addition, nonlinear distortions which are especially pronounced in electromagnetic converters can have an adverse effect on the resulting sound quality. The lack of loudness leads especially to the fact that the audiological indication range for implantation of an electromechanical hearing system can be very limited. This means that patients, for example, with sensorineural hearing loss of greater than 50 dB HL (hearing loss) in the low tone range can only be inadequately supplied with a piezoelectric system. Conversely, pronounced high tone losses can only be poorly supplied with electromagnetic converters. For hearing difficulty bordering on deafness, for the aforementioned reasons implantable electromechanical system have not been used yet. Here, cochlear implants with purely electrical stimulation of the inner ear are used which, of course, do not promise any kind of sound quality which, for example, enables acceptable music transmission, but they are designed primarily for acquiring or restoring sufficient speech understanding as much as possible without lip reading.

The defects of currently available implantable, electromechanical hearing systems, on the one hand, and cochlea implants, on the other, are at least partially circumvented in the latter modified embodiments of the invention because both types of stimulation, i.e., mechanical and electrical stimulation, are used in a single implant system and depending on the individual pathological and audiological situation can be applied in a patient-specific manner. By the combinatorial action of the two forms of stimulation and individually maximized parameter adjustment of the controlling electronic preprocessing system on the one hand an indication position as audiologically wide as possible and on the other hand in individual patients a result as optimum as possible with respect to speech discrimination, sufficient loudness in all relevant spectral ranges and high sound quality can be achieved.

When using the dual intracochlear actuator stimulation arrangement, the indicated stimulator arrangement can advantageously have at least one intracochlear electromechanical converter for direct mechanical stimulation of the inner ear and/or at least one intracochlear hair cell stimulation electrode for indirect mechanical stimulation of the inner ear by electrical stimulation of external hair cells. The cochlear implant electrodes can moreover be used as attenuation elements between adjacent electromechanical converters.

The described system can be designed as monaural or binaural. A binaural system for rehabilitation of a hearing disorder of both ears has two system units which each are assigned to one of the two ears. In doing so the two system units can be essentially identical to one another. But the one system unit can also be designed as a master unit and the other system unit as the slave unit which is controlled by the master unit. The signal processing modules of the two system units can communicate with one another in any way, especially via a wired implantable line connection or via a wireless connection, preferably a bidirectional high frequency section, a solid borne sound-coupled ultrasonic section or a data transmission section which uses the electrical conductivity of the tissue of the implant wearer such that in both system units optimized binaural signal processing and converter array triggering are achieved.

These and further objects, features and advantages of the present invention will become apparent from the following description when taken in connection with the accompanying drawings which, for purposes of illustration only, show several embodiments in accordance with present invention.

DETAILED DESCRIPTION OF THE INVENTION

Figure 1:
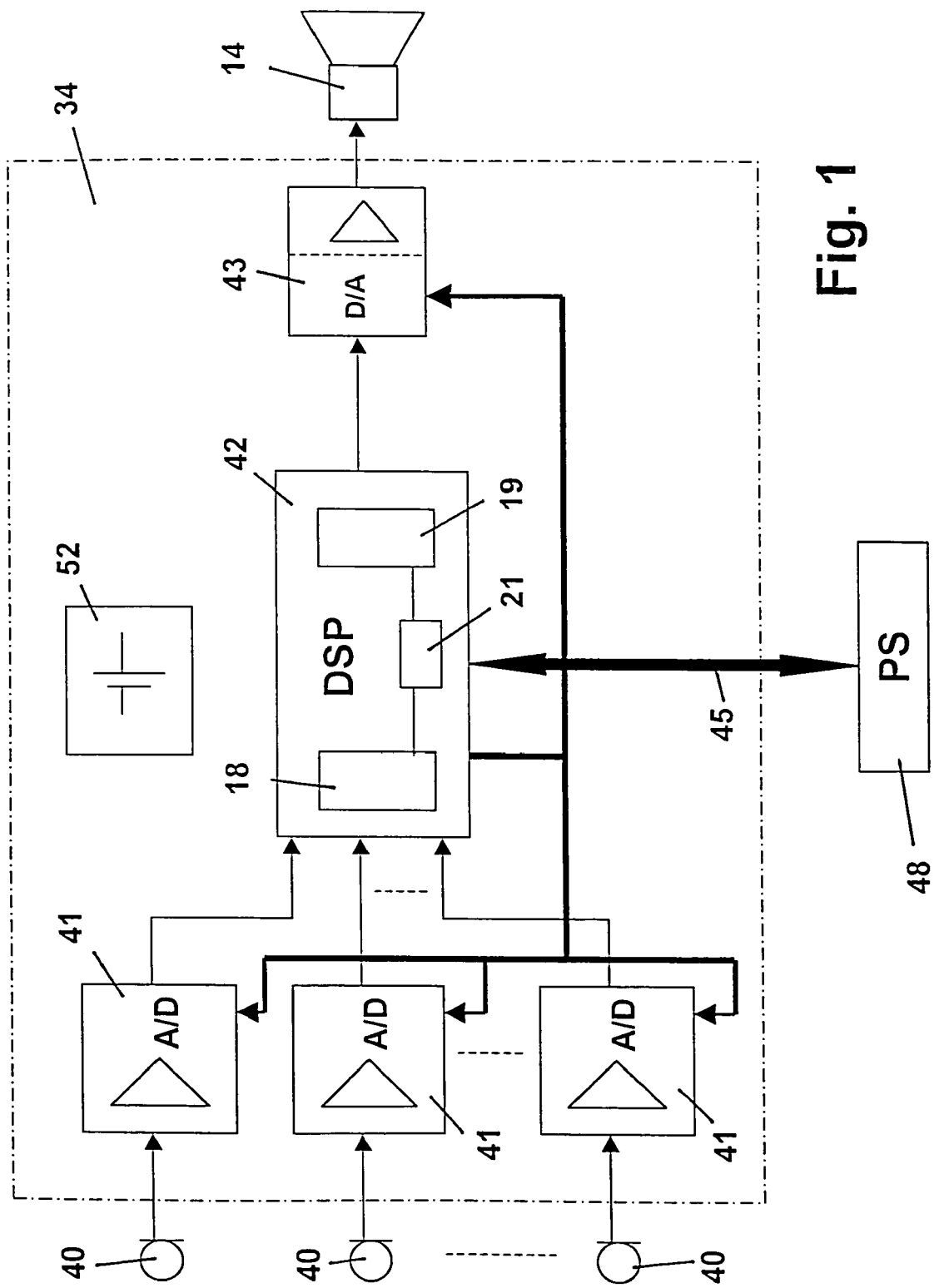
FIG. 1 is a block diagram of an output-side electroacoustic hearing aid with a digital signal processor for signal processing and with a wired programming system.

FIG. 1 shows a block diagram of a nonimplantable hearing aid in which there are one or more acoustic sensors (microphones) 40 which convert the acoustic signal into an analog electrical signal to pick up the external acoustic signals. Downstream of each acoustic sensor 40, a module 41 is connected in which the electrical output signal of the pertinent acoustic sensor 40 is preprocessed, especially pre-amplified, and converted into a digital signal (A/D). The pre-amplification and A/D converter modules 41 are part of an electronic signal processing unit labeled 34 throughout. The signal processing unit 34 includes a digital signal processor 42 (DSP) which further processes the digitized sensor signals and triggers a digital-analog converter (D/A) final amplification module 43. In the module 43, the digital output signal of the signal processor 42 is converted into an analog signal and amplified, and then supplied to an actuator 14 which is made in the conventional manner as an electro-acoustic converter. The electro-acoustic converter can be built, for example, advantageously, in the manner explained in commonly owned, co-pending U.S. patent application Ser. No. 09/465,390, which is hereby incorporated by reference, for sound emission into the external auditory passage and can have an electromechanical converter drive unit which is accommodated in a housing which is hermetically sealed to be gas-tight on all sides and is coupled to a wall of this housing such that output-side mechanical vibrations of the converter drive unit are mechanically directly coupled from the inside to this wall which is made as a bendable membrane and excite the wall to bending vibrations which cause emission of airborne sound outside the converter housing. A control or programming system 48 is assigned by wire to the signal processor 42. Between the signal processor 42 and the control or programming system 48 data can be bidirectionally transmitted via a data bus 45. A power supply unit indicated at 52 supplies the individual components of the system with current.

The signal processor 42 includes, in accordance with the invention, a speech analysis and speech recognition module 18 and a speech synthesis module 19 which are both preferably implemented in the signal processor 42 using software, and are built to be adaptive and/are re-programmable. The speech analysis module 18 undertakes genuine speech information analysis (speech segmentation or speech recognition). Based on the resulting information, in the speech synthesis module 19, a speech output is produced which is based on genuine synthesis. Thus, via the actuator 14 which is made as an electroacoustic converter, a purely artificially produced, synthesized speech signal is output which is essentially without any input-side interference signal portions. At least approximately, the interference signals are completely removed; among other things, this leads to a major improvement of the transmission of speech information in a noisy environment. Processes and devices for speech analysis, speech recognition and speech synthesis as can be fundamentally used here are known from the literature citations named in the introductory part of the specification and therefore do not require detailed explanation here.

Preferably, in the speech analysis module 18, the input signal originating from the pre-amplification and A/D converter modules 41 is analyzed by automatic algorithms based on a digitally implemented neural network and is assigned to phonetic or lexical categories. This phonetic or lexical information represents the input signals for a subordinate speech synthesis module 19. The output signal which is produced therefrom by the speech synthesis module 19 travels, after D/A conversion and the corresponding final amplification in the module 43, to the actuator 14, and it is then transferred to the damaged hearing roughly noise-free by acoustic means. Here, to prevent an especially monotone impression of the re-synthesized speech, it can be a very good idea to extract and transmit information obtained, during analysis, about the emotional state of the speaker or his intention in, for example, question formulations or requests, i.e., in this case, to suitably synthesize them. This additional information is generally called the prosody of the speech. Detection of these prosodic features can comprise, for example, the extraction of the level and the characteristic of the fundamental speech frequency in voiced sounds, such as vowels. During synthesis, the output signal is modulated accordingly in order to transmit this information.

Furthermore, it can be a good idea to provide a module 21 which makes it possible to completely turn off the analysis and synthesis system 18, 19 and to transmit the speech signal or the audio signal like, for example, music in the manner known for conventional hearing aids if there is little or no interfering noise. The module 21 can automatically perform this function depending on the corresponding acquisition of interfering noise or based on a remote control function by the user via the operating or programming system 48.

Figure 2:
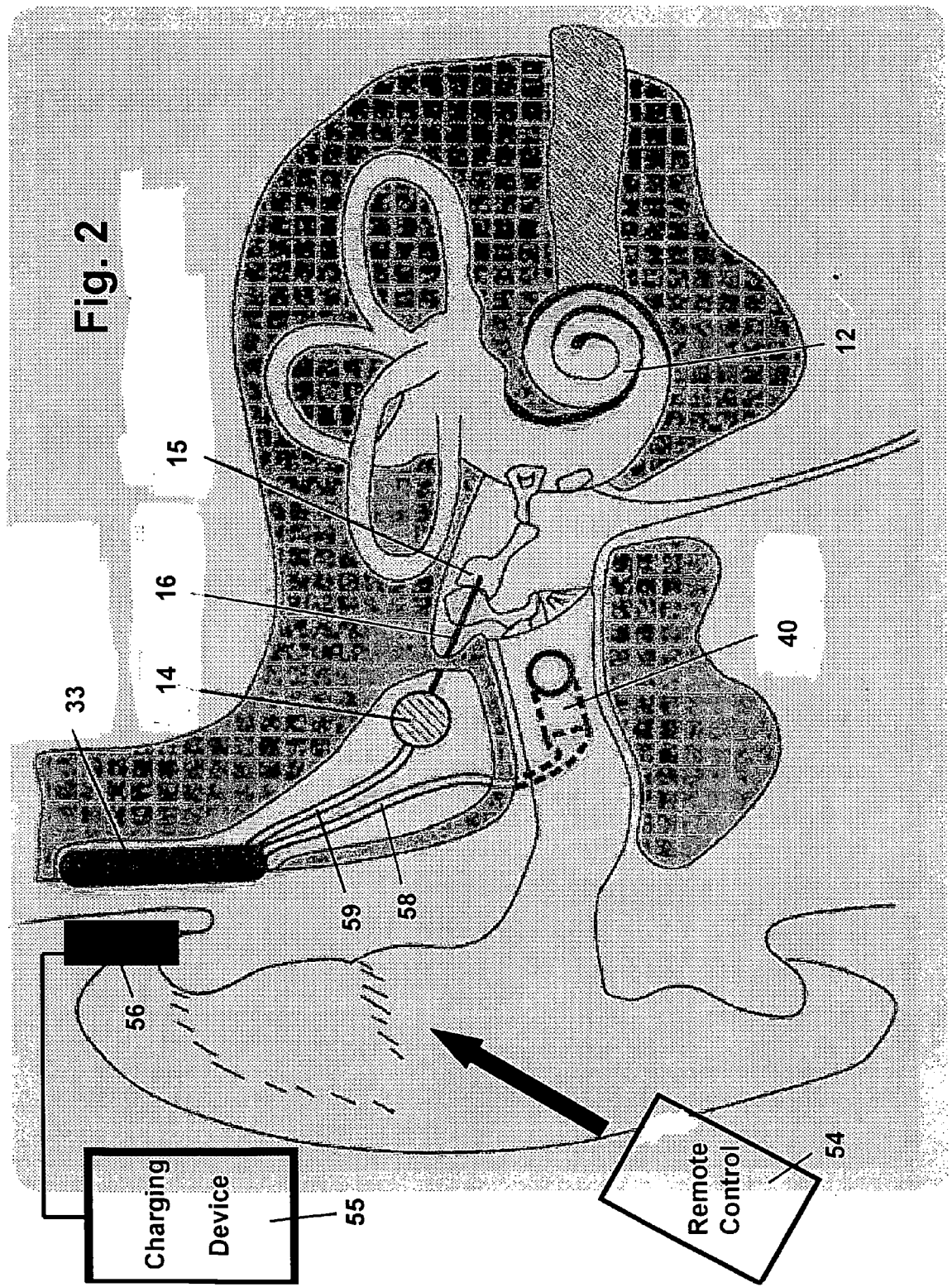
FIG. 2 shows a fully implantable system with an electromechanical converter for middle ear excitation and with a remote control and charging device.

FIG. 2 schematically shows one possible embodiment of a fully implantable hearing system for patients suffering from sensorineural hearing loss with an implantable acoustic sensor (microphone) 40 and an actuator 14 in the form of an electromechanical output converter. Here, provision is made for speech analysis and synthesis which can be activated at least, if necessary, according to FIG. 1. Furthermore, in this hearing system, the operating software can be transcutaneously changed or replaced.

In particular, the system has an electronic module 33 which is accommodated in a hermetically tightly sealed biocompatible housing and which includes the signal processing unit 34 described using FIG. 1, including the speech analysis and speech synthesis modules 18, 19 and preferably also the switching module 21. Furthermore, the implant housing contains, as the power supply unit 52, a secondary, rechargeable element for electrical supply of the implant and a power receiving circuit assigned to this element for making available recharging energy in the implant portion. The implanted power receiving circuit cooperates with the charging device 55 for wireless transcutaneous recharging of the rechargeable element 52 which is located in the implant. One advantageous embodiment of an implantable unit with a charging current feed arrangement is described in published European Patent Application EP 0 984 664 A1. A portable wireless remote control 54 is used to control the implant functions by the implant wearer, data being transferred preferably inductively between the remote control 54 and the electronic module 33.

The microphone 40 can advantageously be built in the manner known from published European Patent Application EP 0 831 673 A2 and can be provided with a microphone capsule which is accommodated hermetically sealed on all sides in the housing, and with an electrical penetration arrangement for routing through at least one electrical terminal from the interior of the housing to its outside, the housing having at least two legs which are aligned at an angle to one another. One leg of the housing holds the microphone capsule and is provided with a sound inlet membrane, while the other housing leg contains the electrical penetration arrangement and is set back relative to the plane of the sound inlet membrane. The geometry of the microphone housing is chosen here such that, when the microphone is implanted in the mastoid cavity, the leg which contains the sound inlet membrane projects from the mastoid into an artificial hole in the anterior bony wall of the auditory passage and the sound inlet membrane touches the skin of the wall of the auditory passage.

To fix the microphone 40, there can be a fixation element of the type known from U.S. Pat. No. 5,999,632 which has a sleeve with which the cylindrical housing part surrounds the leg which contains the sound inlet membrane and is provided with projecting, elastic flange parts which can be placed against the side of the wall of the auditory passage facing the skin of the auditory passage. Here, the fixation element contains preferably a holding device which holds the indicated flange parts before implantation against the elastic restoration force of the flange parts in a bent position which allows penetration through the hole of the wall of the auditory passage.

The charging system also includes a charging coil 56 which is connected to the output of the charging device 55, and which preferably forms part of the transmitting serial resonant circuit in the manner known from U.S. Pat. No. 5,279,292 and can be inductively coupled to the receiving serial resonant circuit which is not shown. The receiving serial resonant circuit can be part of the electronic module 33 in the embodiment as shown in FIG. 2, and according to U.S. Pat. No. 5,279,292, can form a constant current source for the battery 52. Here, the receiving serial resonant circuit is in the battery charging circuit which, depending on the respective phase of the charging current flowing in the charging circuit, is closed via one branch or the other of a full wave rectifier bridge.

The electronic module 33 is connected in the arrangement as shown in FIG. 2 via a microphone line 58 to the microphone 40 and via the actuator feed line 59 to the electromechanical converter 14.

The subcutaneously implanted acoustic sensor 40 (microphone) picks up the sound and converts it into an electrical signal which is supplied via the microphone line 58 to the signal processing unit 34 which forms one part of the electronic module 33. The audiologically processed and amplified signal is routed via the actuator feed line 59 to the electromechanical converter (actuator) 14.

The converter 14 can be built especially in the manner known from published European Patent EP 0 499 940 B1 such that one housing wall of the hermetically tight converter housing is made as a vibrating membrane which together with a piezoelectric ceramic wafer applied to its inside represents an electromechanically active heteromorph composite element and its mechanical vibrations are transmitted to the ossicular chain, in this case, to the anvil 15, via a coupling rod 16 which is permanently attached to the outside of the membrane and optionally a coupling element connected to the coupling rod. The converter vibrations injected there travel via the ossicular chain to the inner ear and there cause the corresponding hearing impression.

The converter 14 can be modified especially in the manner explained in commonly owned, co-pending U.S. patent application Ser. No. 09/311,563, which hereby is incorporated by reference, such that, on the inside of the piezoelectric ceramic wafer, a permanent magnet is attached which interacts in the manner of an electromagnetic converter with an electromagnet coil. This combined piezoelectric-electromagnetic converter is advantageous especially with respect to a wide frequency band and achieving relatively high vibration amplitudes with comparatively small supplied energy.

The converter 14 can also be an electromagnetic converter arrangement as is described in published European Patent Application EP 0 984 663 A1, i.e., a converter arrangement which is provided with a housing which can be fixed at the implantation site with reference to the skull and with a mechanically stiff coupling element which can move relative to the housing, and in which in the housing there is an electromechanical converter with which the coupling element can be caused to vibrate, and which is made as an electromagnet arrangement which has one component which is fixed relative to the housing and one vibrating component which is connected to the coupling element such that the vibrations of the vibrating component are transmitted to the coupling element.

To couple the electromechanical converter 14 to the middle ear or inner ear, especially coupling arrangements as described in U.S. Pat. No. 5,941,814 are suited in which a coupling element, besides the coupling part for the pertinent coupling site, has a crimp sleeve which is first slipped loosely onto a rod-shaped part of the coupling rod 16, which part is provided with a rough surface, and which rod is connected to the converter 14 in the aforementioned manner. During implantation, the crimp sleeve can simply be pushed and turned relative to the coupling rod 16 to exactly align the coupling part of the coupling element with the intended coupling site. Then, the crimp sleeve is fixed by its being plastically cold-deformed by means of a crimping tool.

Alternatively, the coupling element can be fixed with reference to the coupling rod 16 also by means of a belt loop which can be tightened.

Other coupling arrangements which can be preferably used here are described, in particular, in commonly owned, co-pending U.S. patent application Ser. Nos. 09/576,009, 09/626,745, 09/613,560, 09/680,489 and 09/680,488, all of which hereby are incorporated by reference. Thus, according to commonly owned, co-pending U.S. patent application Ser. No. 09/576,009, the coupling element can have a contact surface on its coupling end which has a surface shape which is matched or can be matched to the surface shape of the coupling site, and has a surface composition and surface size such that, by placing the coupling end against the coupling site, dynamic tension-compression force coupling of the coupling element and ossicular chain occur due to surface adhesion which is sufficient for secure mutual connection of the coupling element and the ossicular chain.

The coupling element can be provided with an attenuation element which adjoins the coupling site in the implanted state, with entropy-elastic properties in order to achieve the optimum form of vibration of the footplate of the stapes or the membrane which closes the round window or an artificial window in the cochlea, in the vestibulum or in the labyrinth and especially to minimize the risk of damage to the natural structures in the area of the coupling site during and after implantation (see commonly owned, co-pending U.S. patent application Ser. No. 09/626,745). Additionally, the coupling element can be, according to commonly owned, provided with an adjustment device for selectively moving the coupling element between an open position, in which the coupling element can engage and disengage the coupling site, and a closed positioning, in which the coupling element in the implanted state is connected by force-fit and/or form-fit to the coupling site (see, co-pending U.S. patent application Ser. No. 09/613,560).

Furthermore, for mechanical coupling of the actuator 14, which is made as an electromechanical converter to a pre-selected coupling site on the ossicular chain, the footplate of the stapes or the membrane which closes the round window or an artificial window in the cochlea, in the vestibulum or in the labyrinth (equilibrium organ), a coupling arrangement (see commonly owned, co-pending U.S. patent application Ser. No. 09/680,489) is suitable which has a coupling rod 16 which can be caused to mechanically vibrate by the converter and a coupling element which can be connected to the pre-selected coupling site. The coupling rod and the coupling element are interconnected by at least one coupling and at least one section of the coupling element which adjoins the coupling site in the implanted state is designed for low-loss delivery of vibrations to the coupling site, the first half of the coupling having an outside contour with at least roughly the shape of a spherical dome which can be accommodated in the inside contour of a second coupling half that is at least partially complementary to the outside contour. The coupling has the capacity to swivel and/or turn reversibly against the forces of friction, but is essentially rigid for the dynamic forces which occur in the implanted state.

According to one modified embodiment of this coupling arrangement (see commonly owned, co-pending U.S. patent application Ser. No. 09/680,488) the first half of the coupling has an outside contour with an at least cylindrical, preferably circularly cylindrical, shape which can be accommodated in the inside contour of a second coupling half that is at least partially complementary to the outside contour. A section of the coupling element, which adjoins the coupling site in the implanted state, is designed for low-loss delivery of vibrations to the coupling site in the implanted state, transmission of dynamic forces between the two halves of the coupling taking place essentially in the direction of the lengthwise axis of the first coupling half. The coupling can be reversibly coupled and de-coupled, and can be reversibly moved linearly and/or rotationally with reference to the lengthwise axis of the first coupling half, but is rigid for the dynamic forces which occur in the implanted state.

Figure 3:
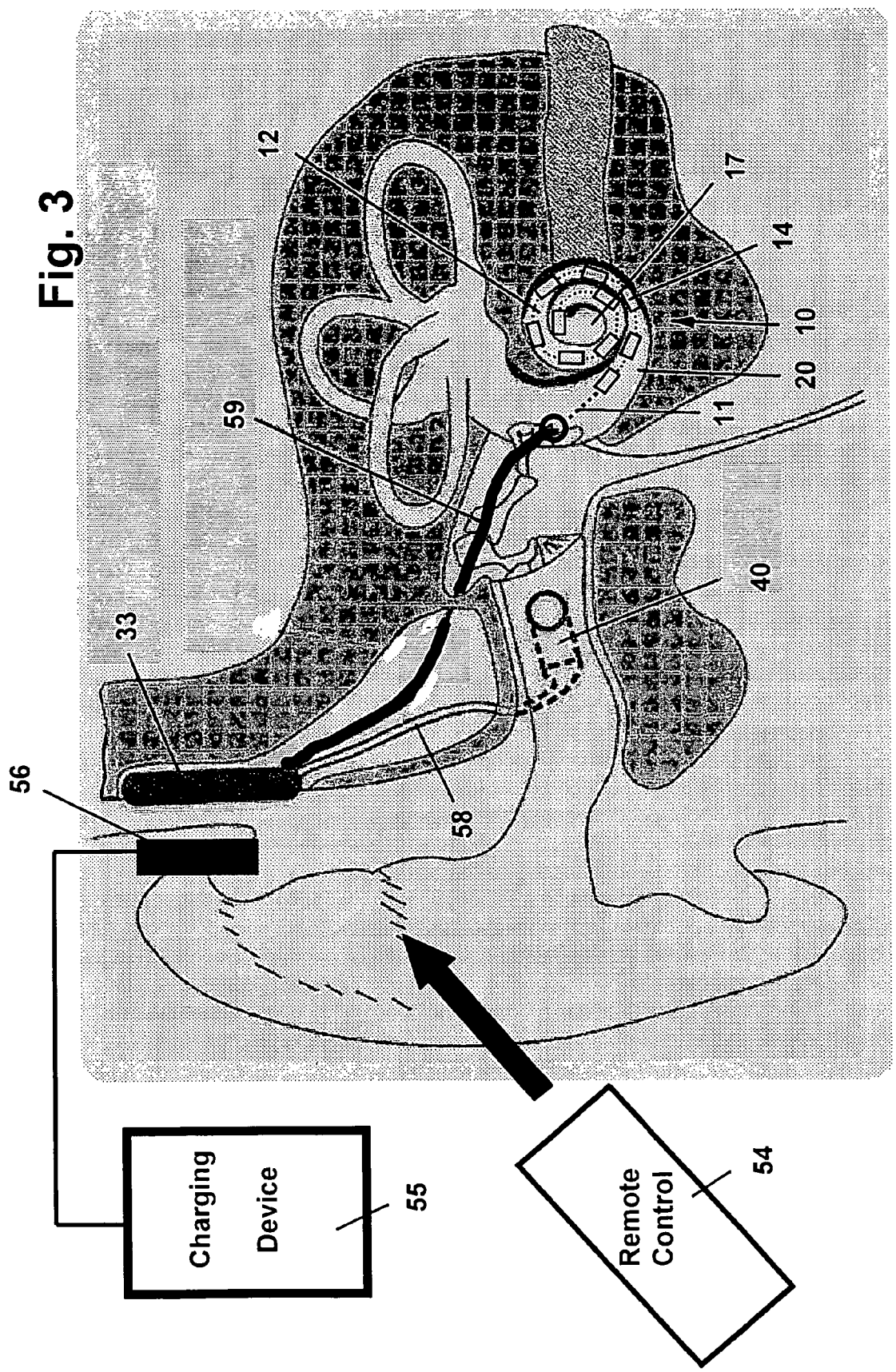
FIG. 3 shows a fully implantable system with several intracochlear electromechanical converters and with a remote control and charging device.

FIG. 3 schematically shows the structure of a fully implantable hearing system similar to FIG. 2, in which there are actuators 14 which form an intracochlear electromechanical converter array 10. The converter array 10 is built similarly to a multichannel intracochlear cochlear implant electrode array. It has a mechanical carrier 11 which preferably is made essentially of a flexible molded part of preferably circular cross section. The molded part is pushed through an artificial opening of the cochlea 12 or the round window into the inner ear. Instead of a distribution of electrical stimulation electrodes of a cochlear implant electrode arrangement along this carrier 11, there are several output-side electromechanical converters located here as actuators 14 which, for example, can be cylindrical elements with a circular cross section. Within the carrier 11, there are electrical feed lines to the converters 14; these feed lines are not shown in detail.

The actuators 14 of the converter array 10 work preferably according to the principle of dynamic volume change as a result of dynamic surface enlargement or reduction according to a triggering electrical converter AC voltage signal. The required volume changes for a suitable equivalent acoustic pressure level of roughly 100 dB SPL are roughly $2 \cdot 10^{-4}$ microliters (see, U.S. Pat. No. 5,772,575).

The actuators 14 are, for example, distributed equidistantly along the carrier 11 or are at logarithmic distances according to the tonotopic location-frequency assignment along the basilar membrane of the inner ear. The total diameter of the converter array arrangement 10 is preferably in the range from 0.4 mm (apical area 17 as shown in FIG. 3) to 2.0 mm (basal area 20 as shown in FIG. 3). The total length of the converter array 10 is feasibly between 5 mm and 50 mm. The actuators 14 are embedded in the carrier 11 for reasons of biocompatibility such that they are completely surrounded by a thin layer of the carrier material. The carrier 11 of the converter array 10 is made of a biocompatible material which is biostable in the inner ear, preferably polymers, such as the corresponding silicones. Between the individual actuators 14, mechanical attenuation elements labeled 22 in FIG. 10 can be embedded in the carrier 11; they minimize the mechanical wave propagation within the carrier to the adjacent converter elements. To achieve high attenuation values, the material of these attenuation elements, with a cross sectional geometry similar to that of the carrier 11, is preferably chosen such that there is a high mechanical impedance difference compared to the carrier material.

The actuators 14 of the converter array 10 can work according to any known electromechanical converter principle, specifically electromagnetic, electrodynamic, piezoelectric, magnetostrictive or dielectric (capacitive). The individual electromechanical converters 14 are advantageously triggered by the signal processing unit 34 of the electronic module 33 such that by the respective choice of the spectral transmission range per converter, the vibratory amplitude and the phase angle of the converters to one another, in the overall actuator result of inner ear stimulation a travelling wave is formed on the basilar membrane which, for the respective external sound event, is as similar as possible to the travelling wave form which would result for an undamaged cochlear amplifier, and thus, with intact external hair cells.

The electronic module 33 which contains the signal processing unit 34, in the arrangement as shown in FIG. 3, is connected via the microphone line 58 to the microphone 40, and via the actuator feed line 59, to the intracochlear converter array 10.

Figure 28:
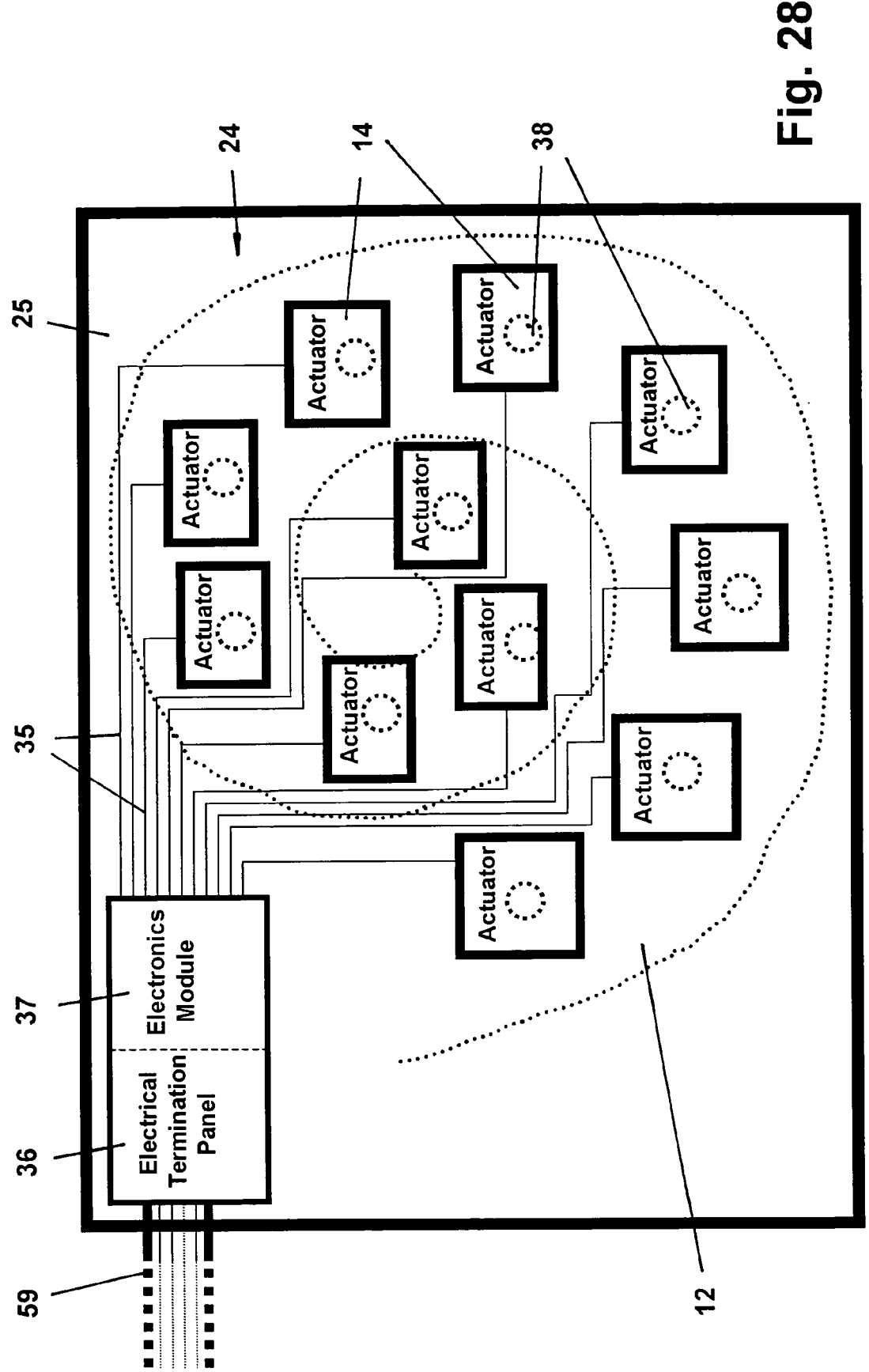

Instead of the intracochlear converter array 10, there can also be an extracochlear array of electromechanical actuators for excitation of the fluid-filled inner ear spaces, as is shown schematically, for example, in FIG. 28. In this electromechanical converter array 24, which is to be applied extracochlearly, several miniaturized output-side actuators 14 in the form of electromechanical converters are placed, via openings or holes made in the bony wall, bordering the cochlea 12 (cochleostomies) such that coupling elements 28 attached on the converter output side project through the cochlear openings into the lymphatic inner ear spaces. Mechanical stimuli of the actuators 14 are produced intracochlearly as volume displacements which lead to a hearing impression. The converter array 24 can preferably be produced with methods of microsystems engineering. On a carrier plate (substrate) 25, there are several converter units 14 (for example, as per International Patent Application Publication WO 99/03146) distributed geometrically as corresponds to the statistical average of the geometrical cochlea dimensions (outline of the cochlea 12 shown by the broken line). At the same time, the substrate 25 contains electrical converter feed lines 35.

Figure 4:
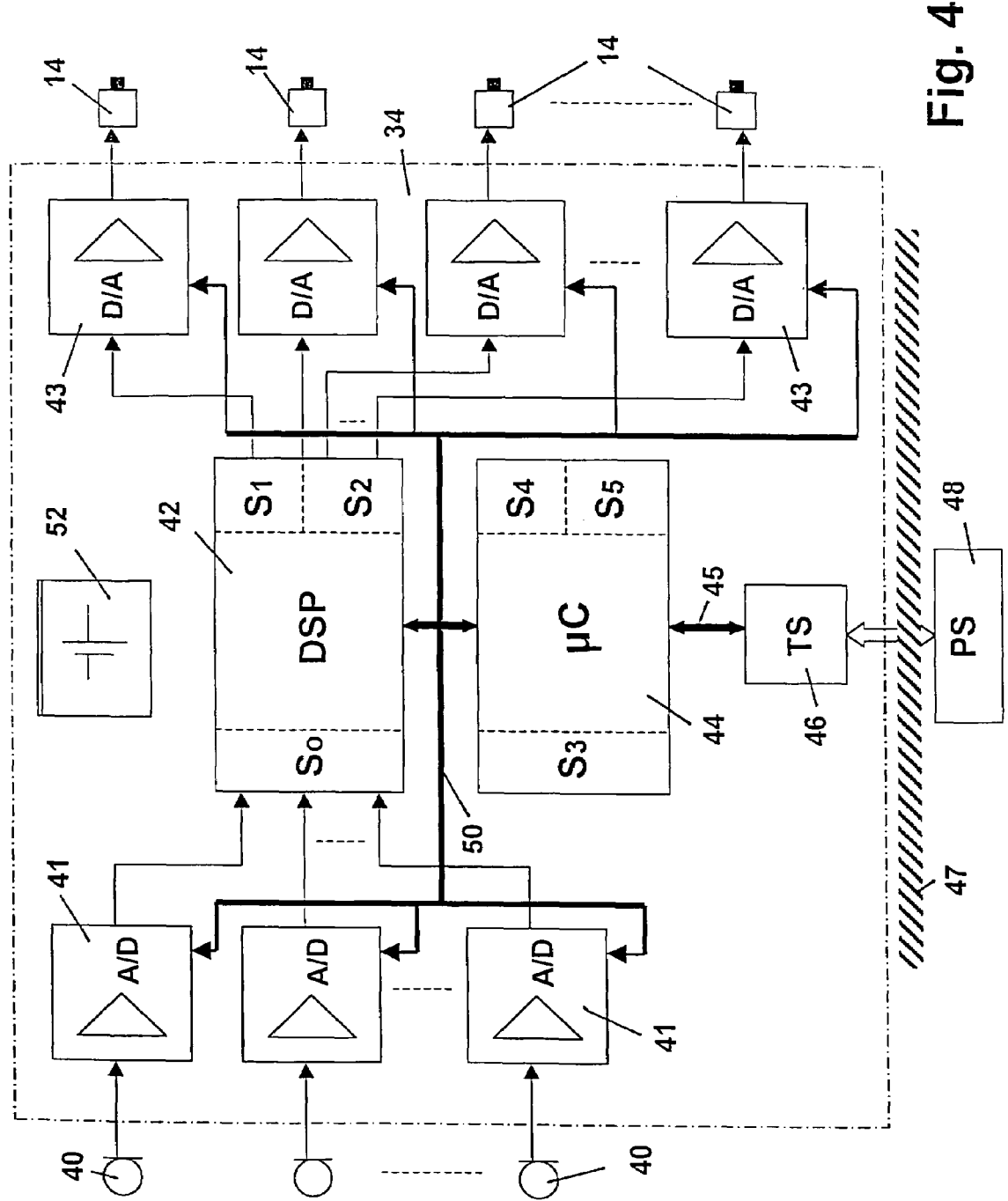
FIG. 4 is a block diagram of a partially or fully implantable system with several electromechanical output converters.

Furthermore, there is an electrical termination panel 36 which is produced at the same time using microsystems engineering and which enables proper connection of a multi-pin, biocompatible implant actuator feed line 59 to the signal processing unit 34 (FIG. 4). In addition, the substrate 25 can contain an electronic module 37 which was produced at the same time using microsystems engineering and which can contain, for example, the driver stages which trigger the actuators 14. Advantageously, this module 37 can also contain decoding logic and converter modules which enable connection of a pin-reduced implant line. Thus, for example, the array terminal can have only three lines, (ground, data, and clock signal), and the necessary supply of electrical operating energy can take place by phantom feed on the clock signal line. The converter-driving signals are then present in digitally coded form and are serially transmitted with a high clock rate. Additionally, an interface module can be contained which enables digital data transmission via the implant line, advantageously by means of an optical fiber. For serial data transmission, the corresponding D/A converters and driver modules which are assigned to the actuators 24 are contained in the electronic module 37. The entire converter array 24, including the carrier structure (substrate) 25, is equipped with biocompatible jacketing which, for example, is made of polymers known from implant technology (polytetrafluorethylene, polyurethane, silicones).

Further details on the hearing system for forming a travelling wave configuration which approximates the type of travelling wave formation of a healthy ear on the basilar membrane are explained in commonly owned, co-pending U.S. patent application Ser. No. 09/833,704, which hereby is incorporated by reference, and can likewise be advantageously used here.

FIG. 4 shows the preferred structure of the signal processing unit 34 for the implantable hearing system as shown in FIG. 3. In this case as well, the external acoustic signal is picked up via one or more acoustic sensors (microphones) 40 and is converted into electrical signals. The analog electrical sensor signals are routed to modules 41 in which they are preprocessed, especially pre-amplified, and converted into digital signals (A/D). This preprocessing can be performed by, for example, analog linear or nonlinear pre-amplification and filtering (for example, anti-aliasing filtration).

The digitized sensor signals are further processed in a digital signal processor 42 (DSP). In this embodiment, the signal processor 42 contains a read-only memory area $S_0$ which cannot be overwritten and in which the instructions and parameters necessary for "minimum operation" of the system are stored, and storage areas $S_1$ and $S_2$ in which the operating software of the intended function or functions of the implant system are filed. The re-writable program storages $S_1$ and $S_2$ for holding the operating software can be based on EEPROM or static RAM cells, and in the latter case, provisions should be made for this RAM area to always be "buffered" by the power supply system within the implant.

The digital output signals of the signal processor 42 are converted in the digital final amplifier modules 43 into analog signals and amplified and then supplied to the output-side electromechanical converters (actuators) 14. The modules 43 can optionally be omitted, if, for example, a pulse-width modulated, serial digital output signal of the signal processor 42 is transferred directly to the actuators 14, for example, in a hearing system with electromagnetic output converters.

The signal processor 42 executes the intended function of the hearing implant. This includes audio signal processing for rehabilitation of a hearing disorder, the speech analysis and speech synthesis discussed using FIG. 1, and optionally, also signal generation in the case of a system with an additional tinnitus masker or noiser function. Furthermore, the digital signal processor 42 contains software modules 18, 19 which are no longer shown individually in FIG. 4 and the following figures, and also preferably the software module 21 as shown in FIG. 1.

Additionally, the digital signal processor 42 contains software modules which effect triggering of the output-side electromechanical converters 14 such that the spectral, time, amplitude-referenced and phase-referenced converter signal properties are dimensioned such that, on the basilar membrane of the damaged inner ear, a traveling wave is produced which approaches as nearly as possible that of healthy hearing. These software modules can be designed to be static and dynamic. A static design is defined as the software modules, based on scientific findings, being stored once in the program storage of the signal processor 42 and remaining unchanged. Dynamic means that these software modules are "able to learn," in order to optimize speech analysis and speech recognition or the desired travelling wave configuration in a time iterative manner. This means that the software modules can be designed to be adaptive, and parameter matching is performed by training the implant wearer, and optionally, using other aids, such as rehabilitation programs.

Speech analysis and speech recognition can advantageously be based on a digitally implemented neural network. Accordingly a software module can also be contained which approximates simulation of a "healthy" cochlear amplifier as optimally as possible based on an adaptive neural network. Training of the neural networks can take place again by the implant wearer and/or using other external aids.

One method for simulation of a "healthy" cochlear amplifier as optimally as possible can be the implementation of the principle of "Time-Reversed Acoustics" (TRA) (Fink, M: "Time-Reversed Acoustics," Scientific American 281:5 (1999), pp. 67-73). Triggering of the output-side actuators 14 takes place by TRA such that locally limited areas of the cochlea are mechanically stimulated. While in conventional applications of TRA, the registration of the distributed sound event and the emission of the time-reversed signal take place in the same preparation, these two steps are separated in this case. The distributed events can be determined intracochlearly, for example, in a suitable animal model; then, the time-reversed stimuli in this application of a hearing system are applied to humans, optionally with parameter matching to the altered geometry of the human cochlea.

So that the software-based algorithms for speech analysis and recognition and simulation of the cochlear amplifier as optimally as possible, especially in a full implant, can also be implemented postoperatively, the system as shown in FIG. 4 contains another microprocessor module, for example, a microcontroller (μC) 44 with pertinent storages ($S_3$, $S_4$, $S_5$). The storage $S_3$ is a re-writable storage in which the working program for the microcontroller 44 is stored. Especially the operating software portions of the implant management system (for example, administration monitoring and telemetry functions) can be stored in the storage areas $S_4$ and $S_5$. Storages $S_1$ and/or $S_2$ and/or $S_4$ and/or $S_5$ can also store patient-specific, for example, audiological adaptation parameters, which can be altered from the outside.

On the one hand, the microcontroller 44 communicates via a bidirectional data bus 45 and a telemetry system (TS) 46 wirelessly (for example, via inductive coupling) through the closed skin indicated at 47 with an external programming system (PS) 48. The programming system 48 can be a PC-based system with the corresponding programming, processing, display and administration software. Via this telemetry interface the operating software of the implant system which is to be changed or completely replaced is transmitted and buffered first of all in the storage area $S_4$ and/or $S_5$ of the microcontroller 44. Thus, for example, simple verification of software transmission can be performed by a reading process via the telemetry interface before the operating software or the corresponding signal processing portions of this software are transmitted into the program storage areas $S_1$ and $S_2$ of the digital signal processor 42 via the data bus 50. Furthermore, the working program for the microcontroller 44 can be changed or replaced in whole or in part via the telemetry interface using the external unit 48.

On the other hand, the microcontroller 44 controls the A/D converter modules 41 for sensor preprocessing, the D/A converter modules 43 for triggering the electromechanical converters 14 and the signal processor 42 itself within the implant via the bidirectional data bus 50. Via the data bus 50, program parts or entire software modules can also be transferred between the outside world, the microcontroller 44 and the signal processor 42.

In the fully implanted embodiment, the implant system contains, as the power supply unit 52, a primary or secondary battery cell which supplies the individual modules with electrical operating energy.

Figure 5:
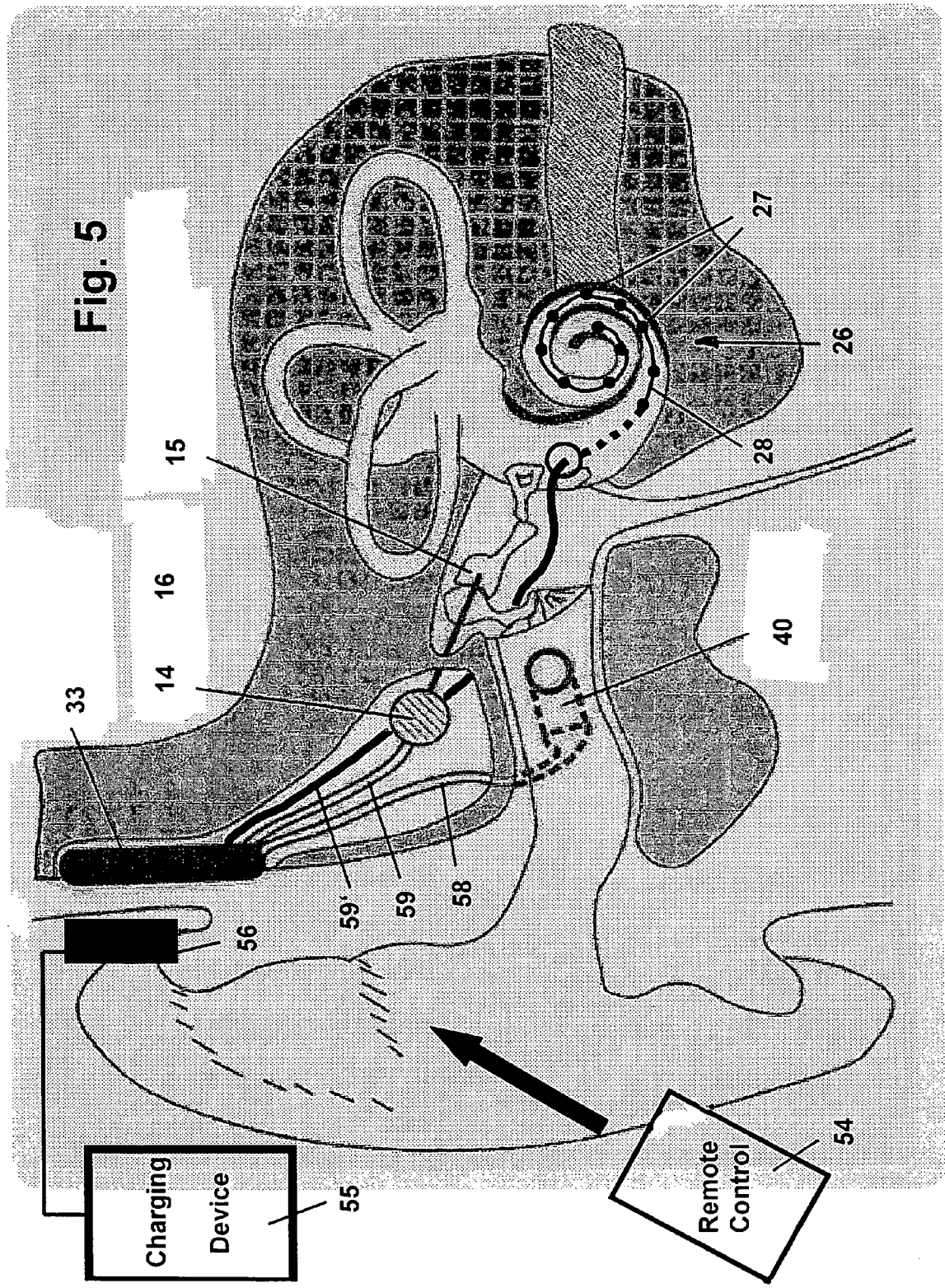
FIG. 5 shows a fully implantable system with an electromechanical converter for middle ear excitation and several intracochlear electrical stimulation electrodes and with remote control and charging devices.

FIG. 5 schematically shows the structure of a completely implantable hearing system with an output-side actuator stimulation arrangement which has an electrical intracochlear array 26 as with several stimulation electrodes 27 and an electromechanical converter 14 which is coupled here, for example, via the coupling rod 16 to the anvil 15.

The intracochlear stimulation electrode array 26 can be built in any manner known for cochlear implants, for example, as a unipolar or bipolar arrangement. It has an electrode carrier 28 of electrically insulating, flexible material along which the stimulation electrodes 27 which are connected to the feed lines 59' are arranged distributed at a mutual distance. The stimulation electrodes 27 are embedded in the carrier 28 or are fixed on the carrier 28 such that a portion of the surface per stimulation electrode is in direct galvanic contact with the lymphatic fluid of the inner ear or directly with one of the neural structures to be stimulated.

The actuator 14 can be designed in the manner explained above with reference to FIG. 2 and can be coupled to the middle ear or inner ear. Reference is also made to the preceding description of FIG. 2 with reference to the acoustic sensor 40, the wireless remote control 54 and the charging device 55.

Figure 6:
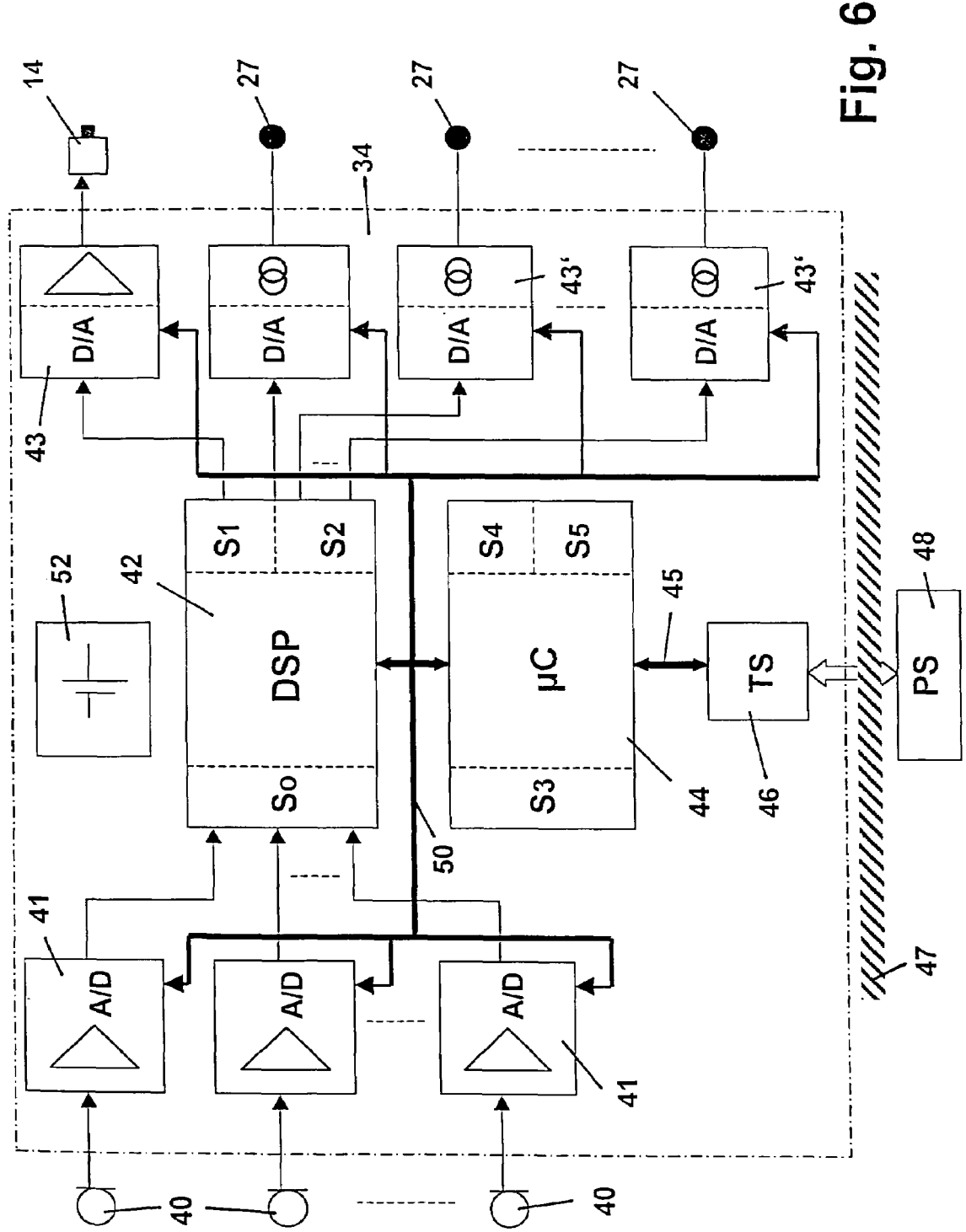
FIG. 6 is a block diagram of a partially or fully implantable system with an electromechanical converter and several electrical stimulation electrodes.

FIG. 6 shows a preferred embodiment of the signal processing unit 34 for the implantable hearing system as shown in FIG. 5. The digital signal processor 42 contains software modules which undertake dual triggering of the stimulation electrode array 26 and the individual stimulation electrodes 27 and the electromechanical converter 14 such that the spectral, time, amplitude-referenced and phase-referenced converter or stimulating electrode signal properties are configured such that optimum hearing success is approximated for the pertinent patient. The D/A converter modules 43', which are connected upstream of the stimulation electrodes 27 and which like the D/A converter module 43 assigned to the electromechanical converter 14 are supplied with the digital output signals of the signal processor 42, comprise, as shown in FIG. 6, a respective digitally controlled current source for supplying current to each of the pertinent stimulation electrodes 27. Otherwise, the structure and function of the circuit as shown in FIG. 6 matches those of the embodiment as shown in FIG. 4.

Other details of a hearing system with combined stimulation of the middle ear or inner ear via an actuator in the form of an electromagnetic converter and electrical stimulation of the inner ear by means of an intracochlear, electrically acting stimulation electrode array are explained in commonly owned co-pending U.S. patent application Ser. No. 09/833,643, which hereby is incorporated by reference, and can likewise be advantageously used here.

Figure 7:
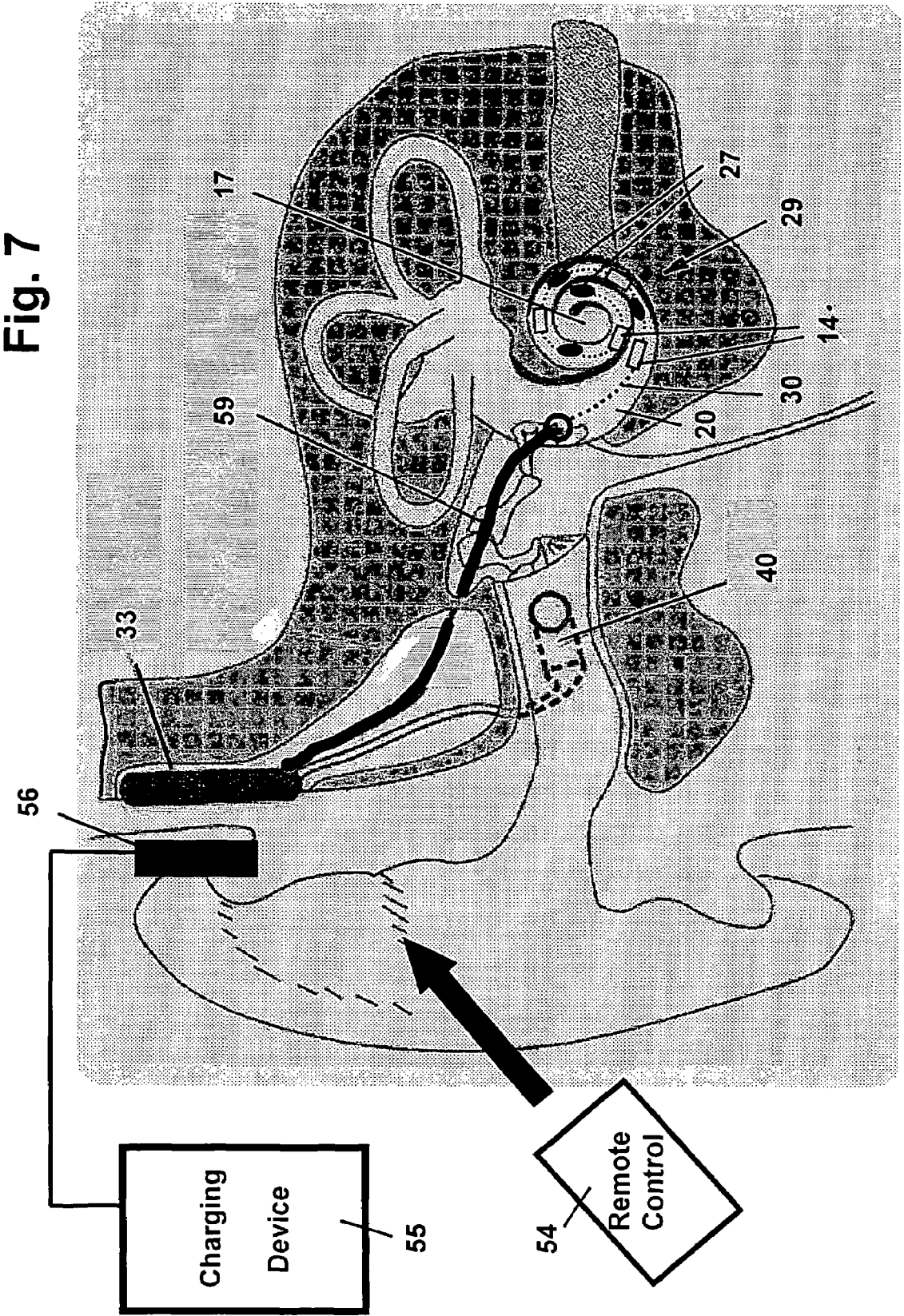
FIG. 7 shows a fully implantable system with several intracochlear electromechanical converters and several intracochlear electrical stimulation electrodes and with remote control and charging devices.

FIG. 7 schematically shows an implantable hearing system similar to that of FIGS. 3 & 5 in which, however, in contrast thereto, the actuator arrangement is an intracochlear dual stimulation array 29 with several cochlear implant stimulation electrodes 27 for direct electrical stimulation of the inner ear and with several intracochlear actuators 14 in the form of electromechanical converters for direction mechanical stimulation of the inner ear in a common mechanical carrier 30. Fundamentally, this array 29 is built similarly to a multichannel intracochlear cochlear implant electrode array, and it is connected via the converter array feed line 59 to the electronic module 33. The carrier 30 preferably is comprised essentially of a flexible silicone molded part of preferably circular cross section. The molded part is pushed through the oval window, the round window or an artificial opening of the cochlea 12 or into the fluid-filled inner ear spaces. The electromechanical converters 14 are shown schematically in FIG. 7 as cylindrical elements with a likewise circular cross section. Within the carrier 30 there are electrical feed lines to the cochlear implant electrodes 27 and the converters 14; these individual feed lines are not shown in detail.

The electromechanical converters 14 of the dual array 29 work preferably according to the principle of dynamic volume change as a result of dynamic surface enlargement or reduction according to a triggering electrical converter AC voltage signal. The converters 14 are, for example, distributed equidistantly along the carrier 30 or at logarithmic distances according to the tonotopic location-frequency assignment along the basilar membrane of the inner ear. The total diameter of the converter electrode arrangement 29 is preferably in the range from 0.4 mm (apical area 17 as shown in FIG. 7) to 2.0 mm (basal area 20 as shown in FIG. 7). The total length of the stimulation array 29 is feasibly between 5 mm and 50 mm. The electromechanical converter elements 14 are embedded in the carrier 30 for reasons of biocompatibility such that they are completely surrounded by a thin layer of carrier material. The carrier 30 of the stimulation array 29 is made of a biocompatible material which is biostable in the inner ear, preferably polymers, such as the corresponding silicones.

The cochlear implant electrodes 27, as known in cochlear implants, are embedded in the carrier 30 or are fixed in or on the carrier 30 such that a portion of the surface per stimulation electrode is in direct galvanic contact with the lymphatic fluid of the inner ear or directly with one of the neural structures to be stimulated. The cochlear implant electrode 27 can be made of all known biocompatible metals, especially pure platinum, preferably platinum-iridium alloys (preferably 90% Pt, 10% Ir), pure gold, gold alloys, tantalum, tantalum alloys, niobium, niobium alloys and high quality steels.

Advantageously, the electromechanical converters 14 and the cochlear implant electrodes 27 alternate with one another in the lengthwise direction of the carrier 30 so that mechanical wave propagation within the carrier 30 between adjacent electromechanical converter elements 14 can be damped and locally concentrated mechanical stimulation per converter is achieved.

Other details of the dual intracochlear stimulation array 29 which is suitable here are explained in commonly owned co-pending U.S. patent application Ser. No. 74/833,643, which hereby is incorporated by reference. Otherwise, the arrangement of FIG. 7 corresponds to the embodiments described using FIGS. 3 & 5.

Figure 8:
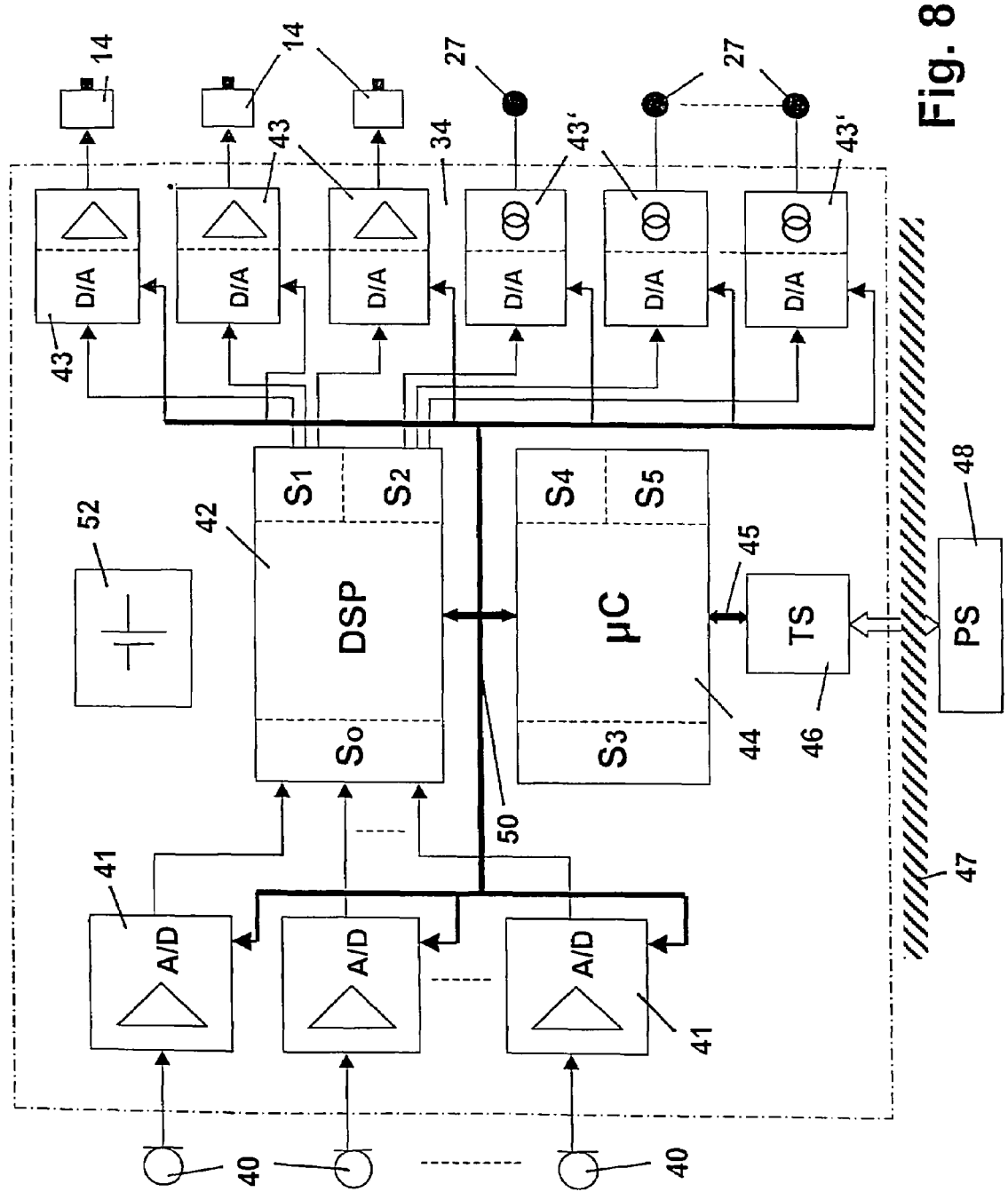
FIG. 8 is a block diagram of a partially or fully implantable system with several electromechanical converters and several electrical stimulation electrodes.

A design of the signal processing unit 34 contained in the electronic module 33 which is suitable for the embodiment of FIG. 7 is shown in FIG. 8. As shown there, the actuators 14 of the dual intracochlear stimulation array 29 which are made as electromechanical converters are each triggered by the digital-analog converter final amplification module 43, while to supply power to the stimulation electrodes 27 of the array 29, there is a digital-analog converter module 43' with a digitally controlled power source. Otherwise, the structure and function of the circuit as shown in FIG. 8 agree with those of the embodiments shown in FIGS. 4 & 6.

Figure 9:
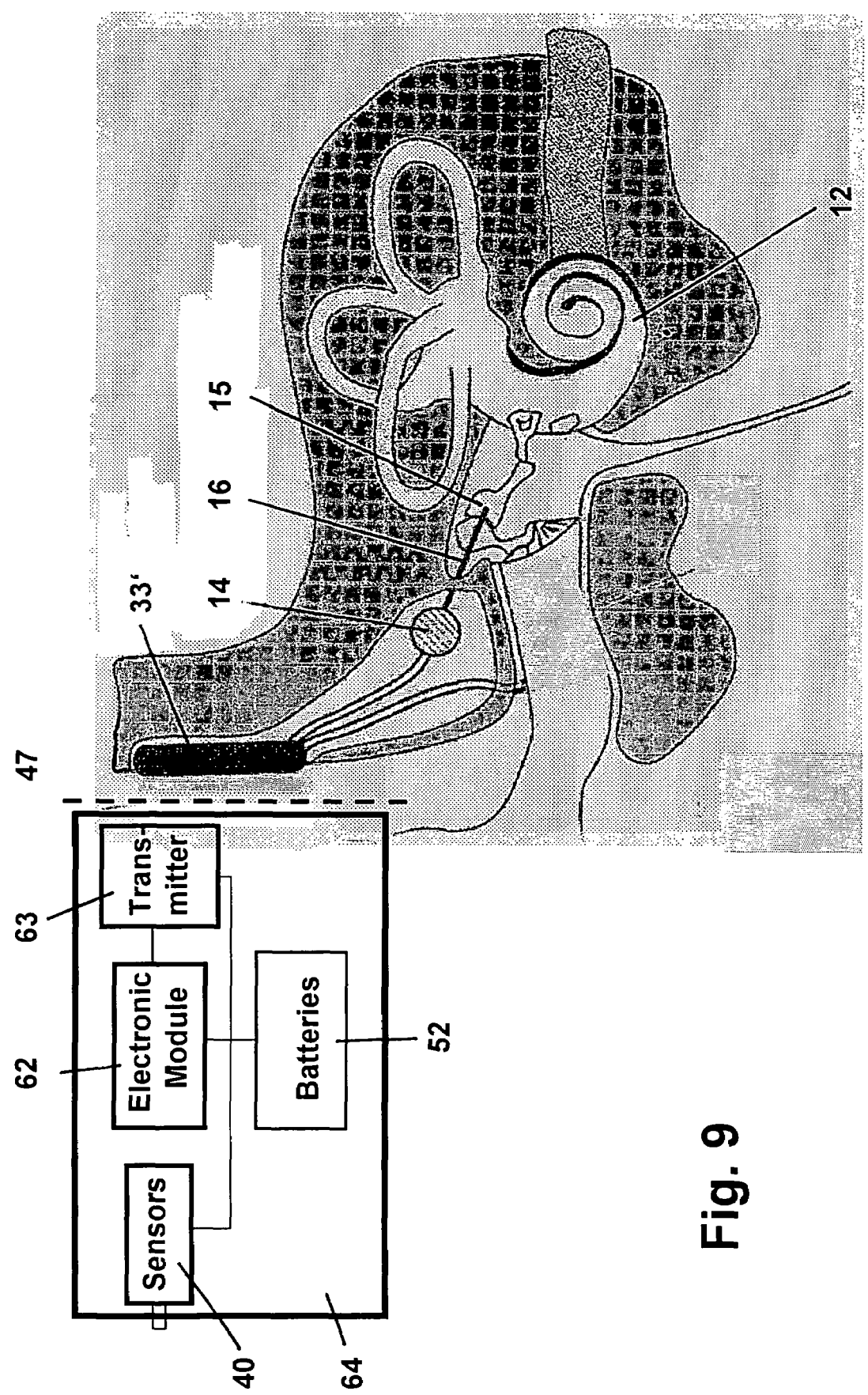
FIG. 9 shows a partially implantable system with an electromechanical converter for middle ear excitation.
Figure 10:
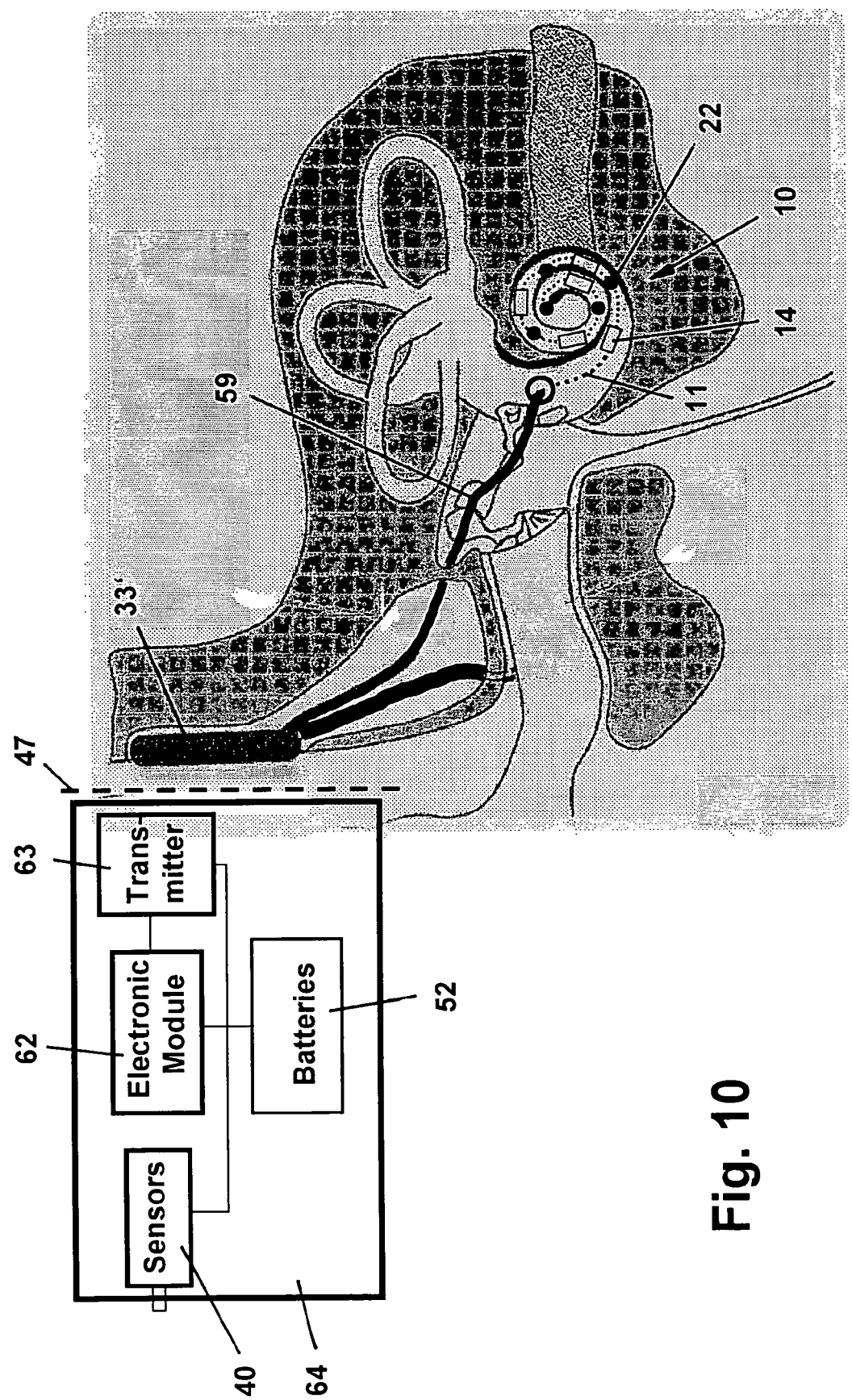
FIG. 10 shows a partially implantable system with several intracochlear electromechanical converters.
Figure 11:
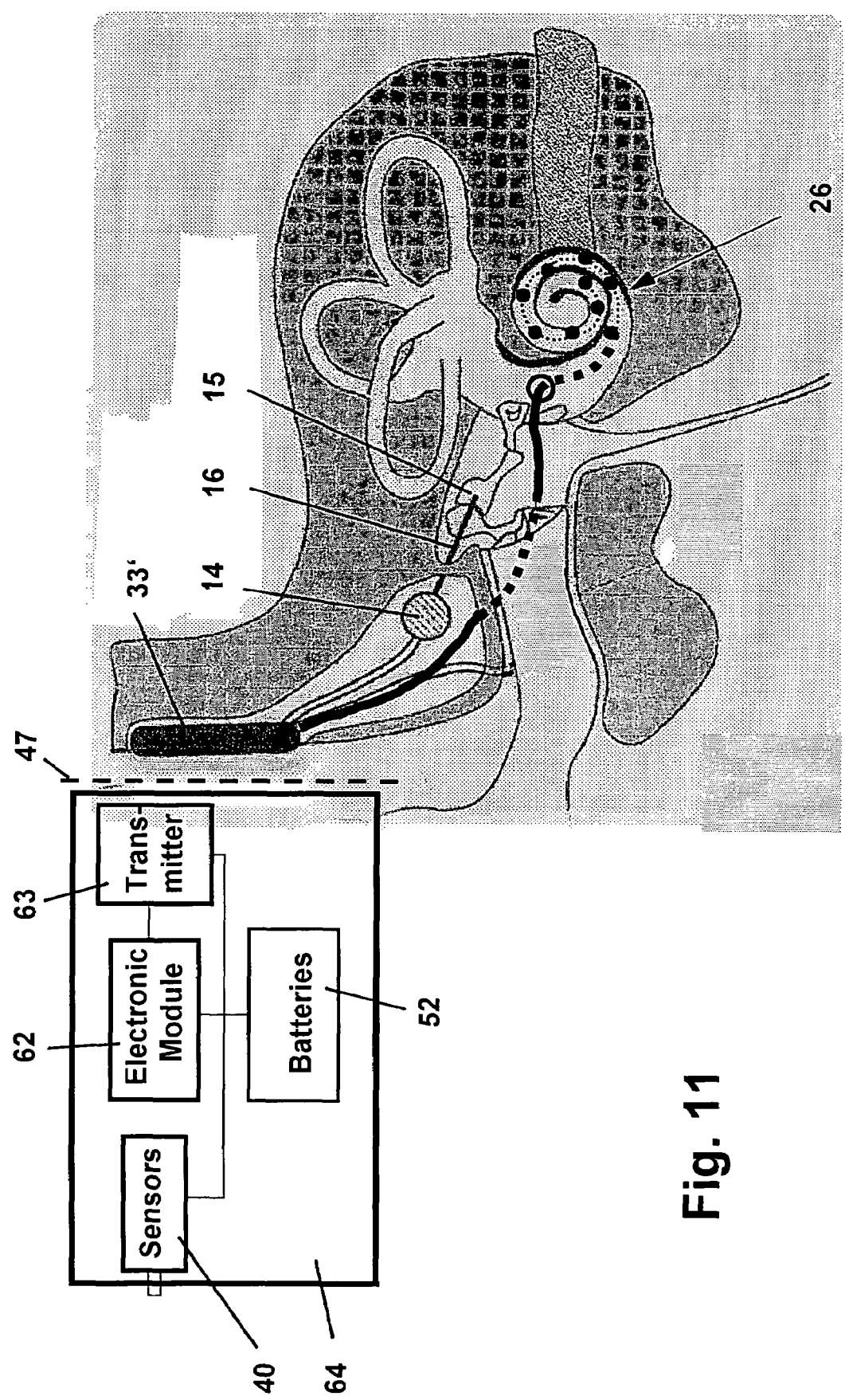
FIG. 11 shows a partially implantable system with an electromechanical converter and several intracochlear electrical stimulation electrodes, FIGS. 12 to 15 each show a fully implantable binaural system with a line connection between the two electronic modules and with different actuator arrangements, FIGS. 16 to 19 each show a fully implantable binaural system with a wireless connection between the two electronic modules and with different actuator arrangements, FIGS. 20 to 23 each show a fully implantable binaural system with ultrasonic coupling between the two electronic modules and with different actuator arrangements, FIGS. 24 to 27 each show a fully implantable binaural system with coupling of the two electronic modules by means of a modulated tissue current and with different actuator arrangements, and FIG. 28 schematically shows one embodiment for the structure of an extracochlear electromechanical converter array.
Figure 12:
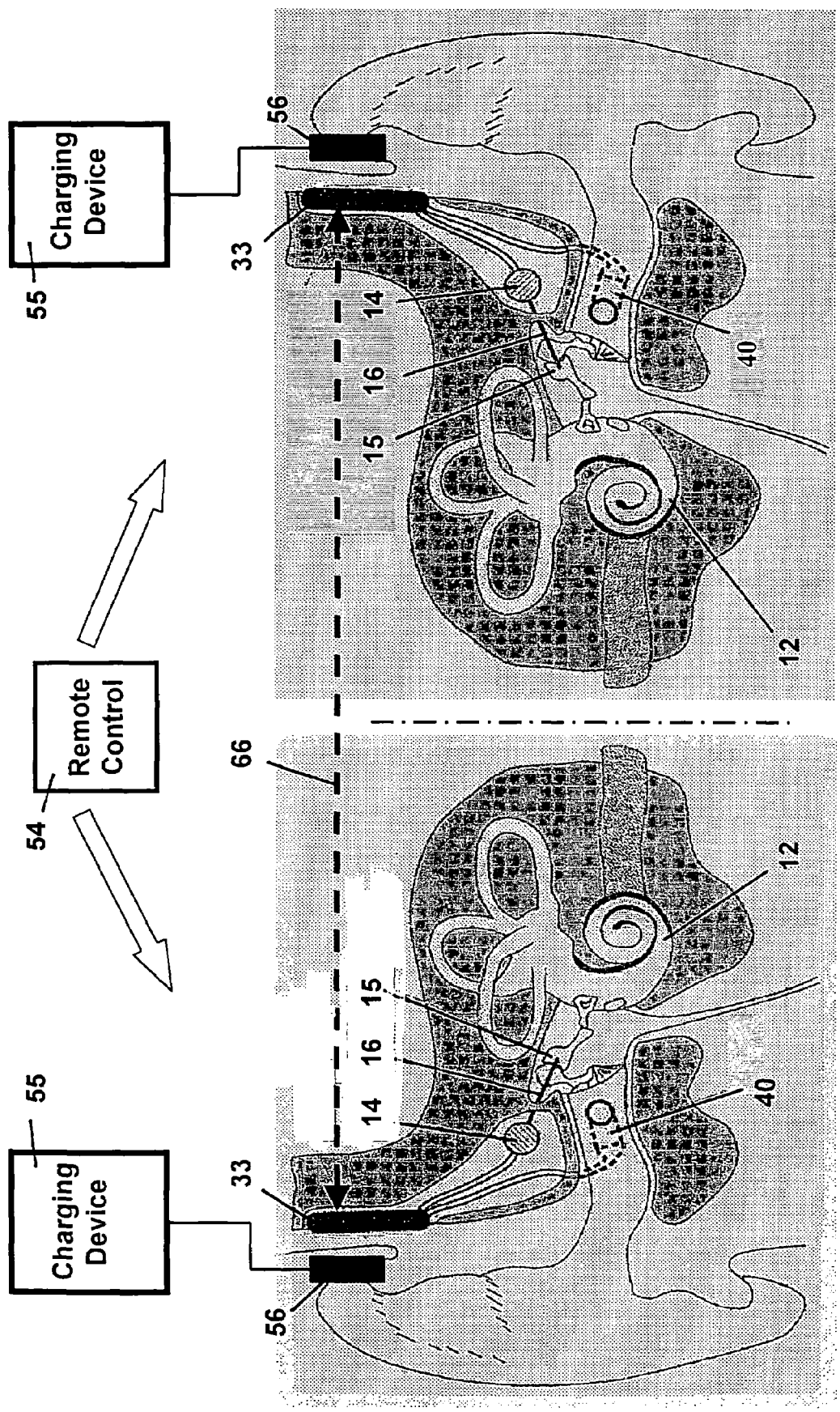
Figure 13:
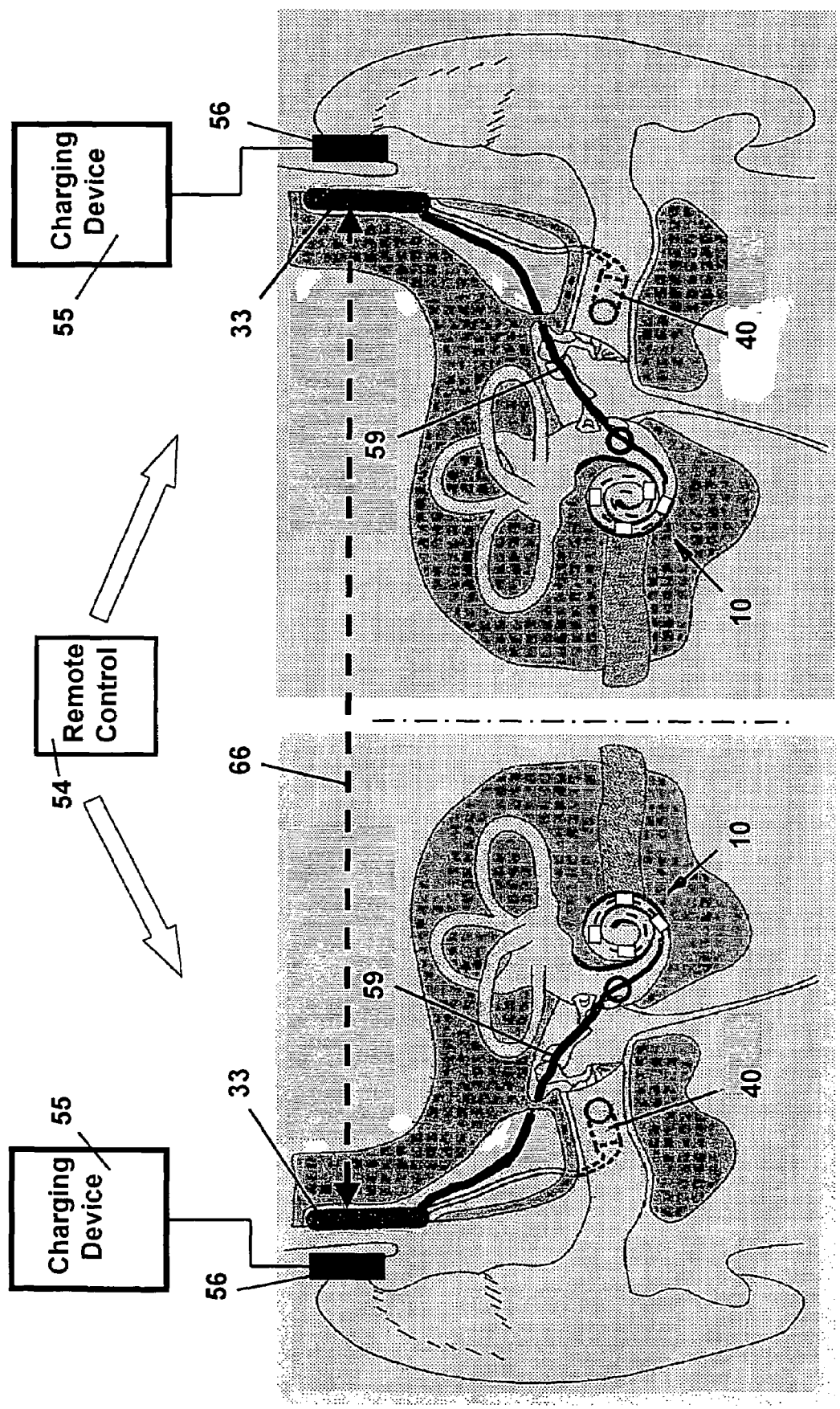
Figure 14:
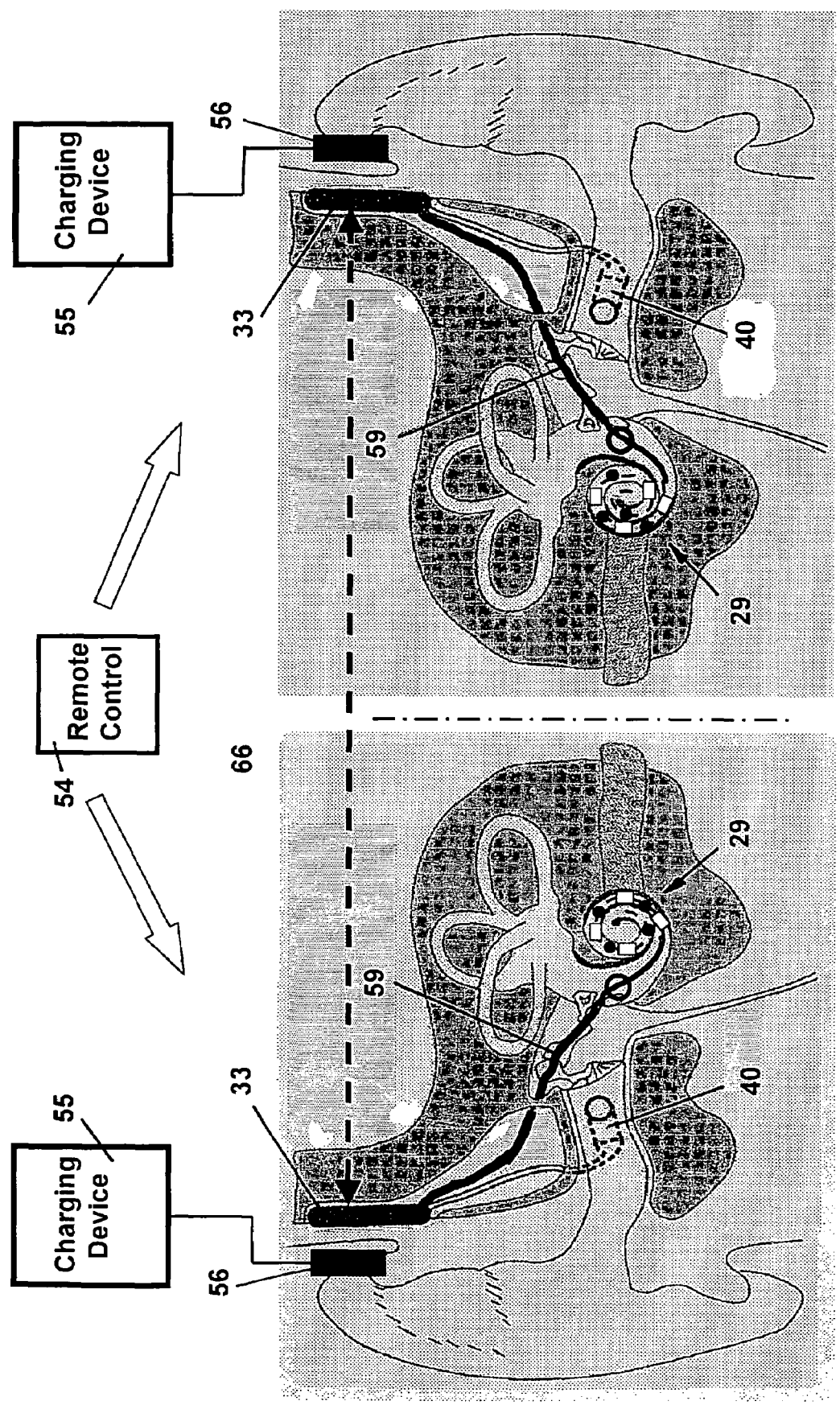

FIGS. 9, 10 and 11 schematically show the structure of a partially implantable hearing system with an actuator arrangement as shown in FIG. 2, FIG. 3 and FIG. 5, respectively. In these partially implantable systems, at least one acoustic sensor (microphone) 40, an electronic module 62 for electronic signal processing for the most part according to FIGS. 1, 4 & 6, respectively (but without the telemetry system 46), the power supply 52 and a modulator/transmitter unit 63 are contained in an external module 64 which can be worn externally on the body, preferably on the head over the implant. The implant is passive in terms of energy, like known partial implants. Its electronic module 33' (without the power supply 52) receives its operating energy and converter control data via the modulator/transmitter unit 63 in the external part 64. It goes without saying that in such a partially implantable hearing system there can also be a dual intracochlear stimulation array 29 as shown in FIG. 7, and that a binaural application analogous to the embodiments described below is possible.

Figure 15:
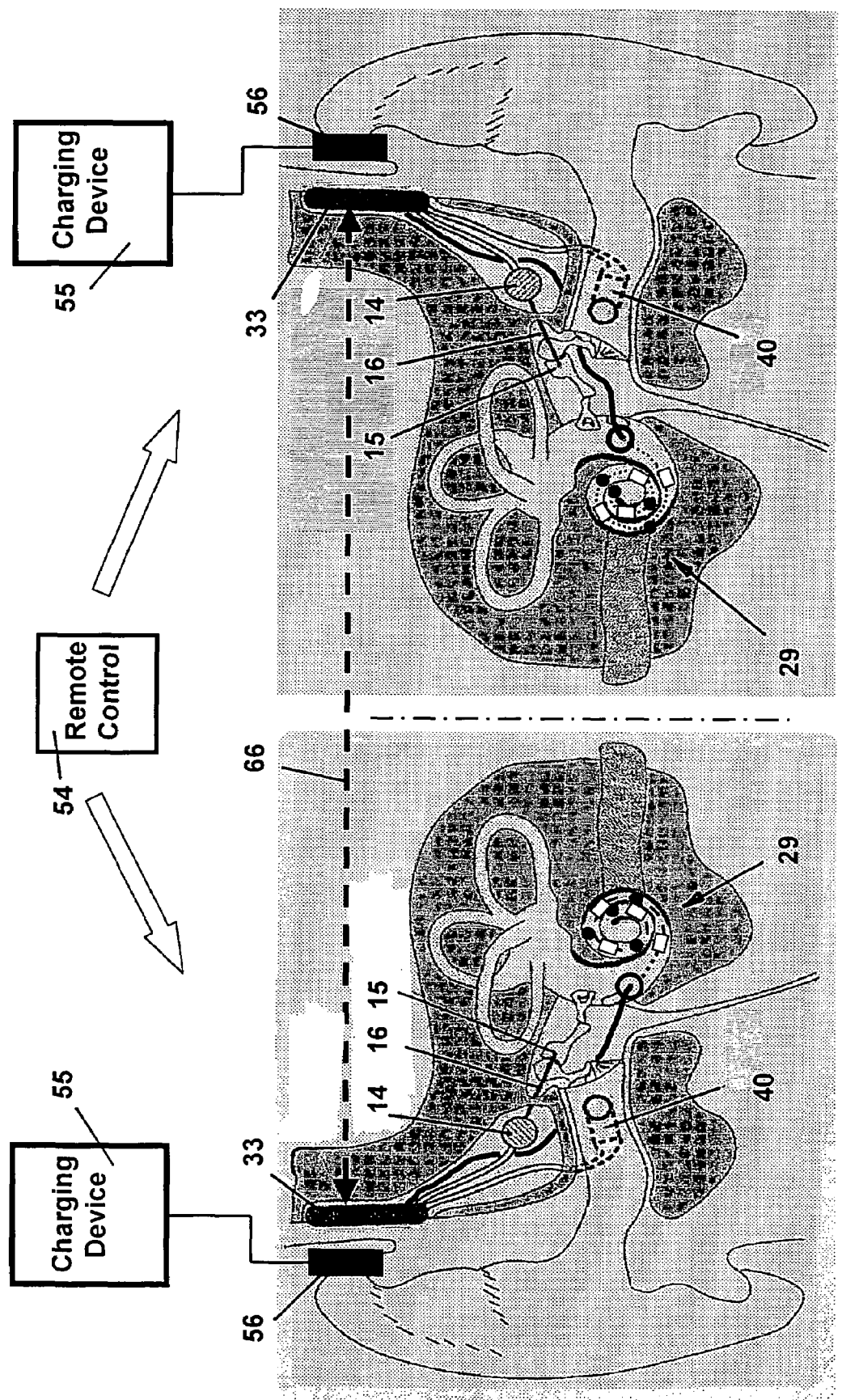

FIGS. 12, 13, 14, & 15 each show a binaural application of a hearing implant in which the signal processing units 34 in the electronic modules 33 on both sides of the skull communicate with one another via a wired implantable line connection 66 such that optimum binaural sensor signal processing and actuator triggering in the two inner ears which have been provided with implants are achieved. Furthermore, there are also transcutaneous charging devices 55, 56 here for the case of implant-side secondary energy storage elements (batteries 52) and a wireless remote control 54 which synchronously controls the two electronic modules 33 for use by the implant wearer. In the case of the embodiments of FIGS. 12, 13, & 14, the actuator arrangements are designed as shown in FIGS. 2, 3 & 7, respectively. FIG. 15 shows an embodiment in which the dual intracochlear stimulation array 29 as shown in FIG. 7 is combined with an actuator 14 as shown in FIG. 2.

Figure 16:
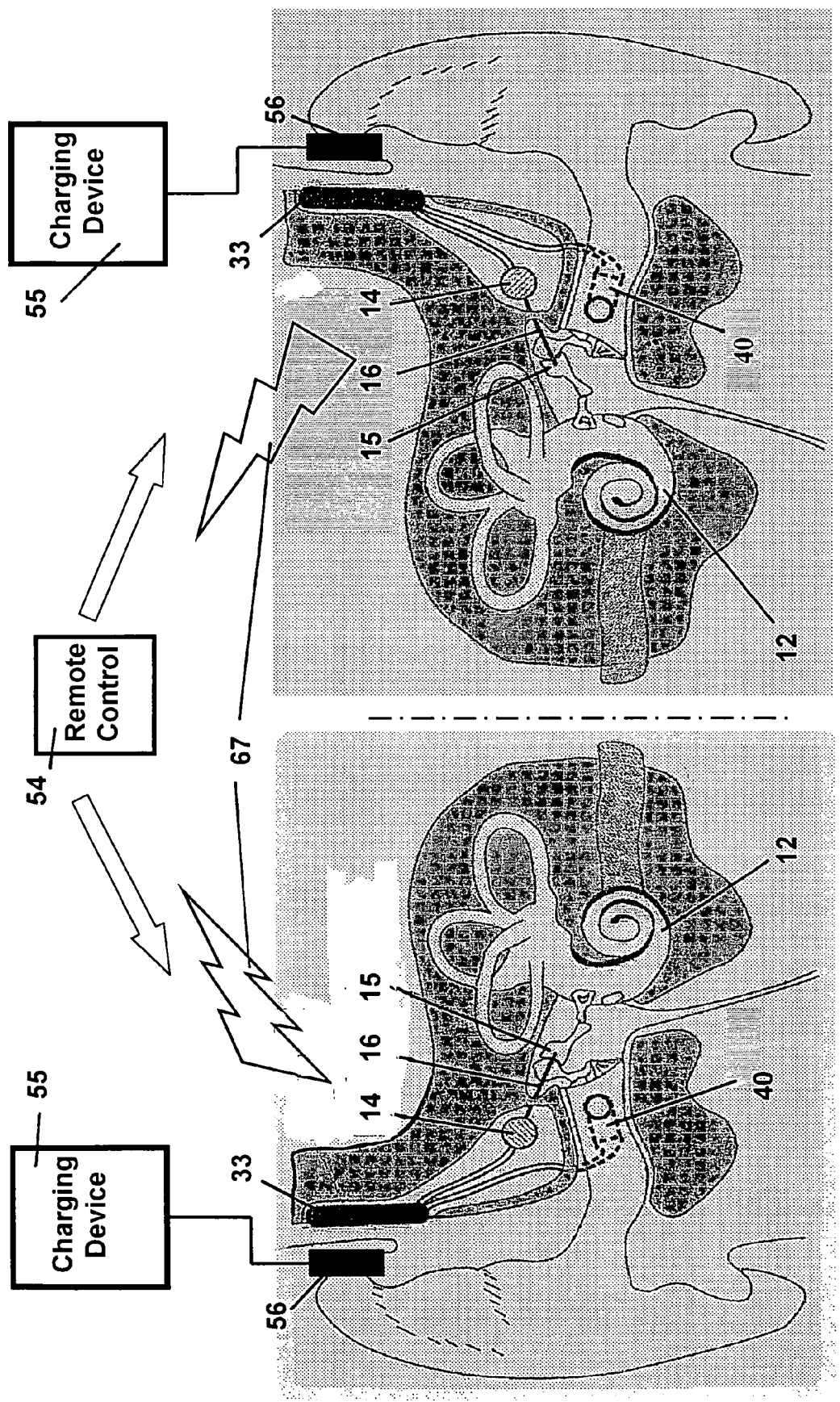
Figure 17:
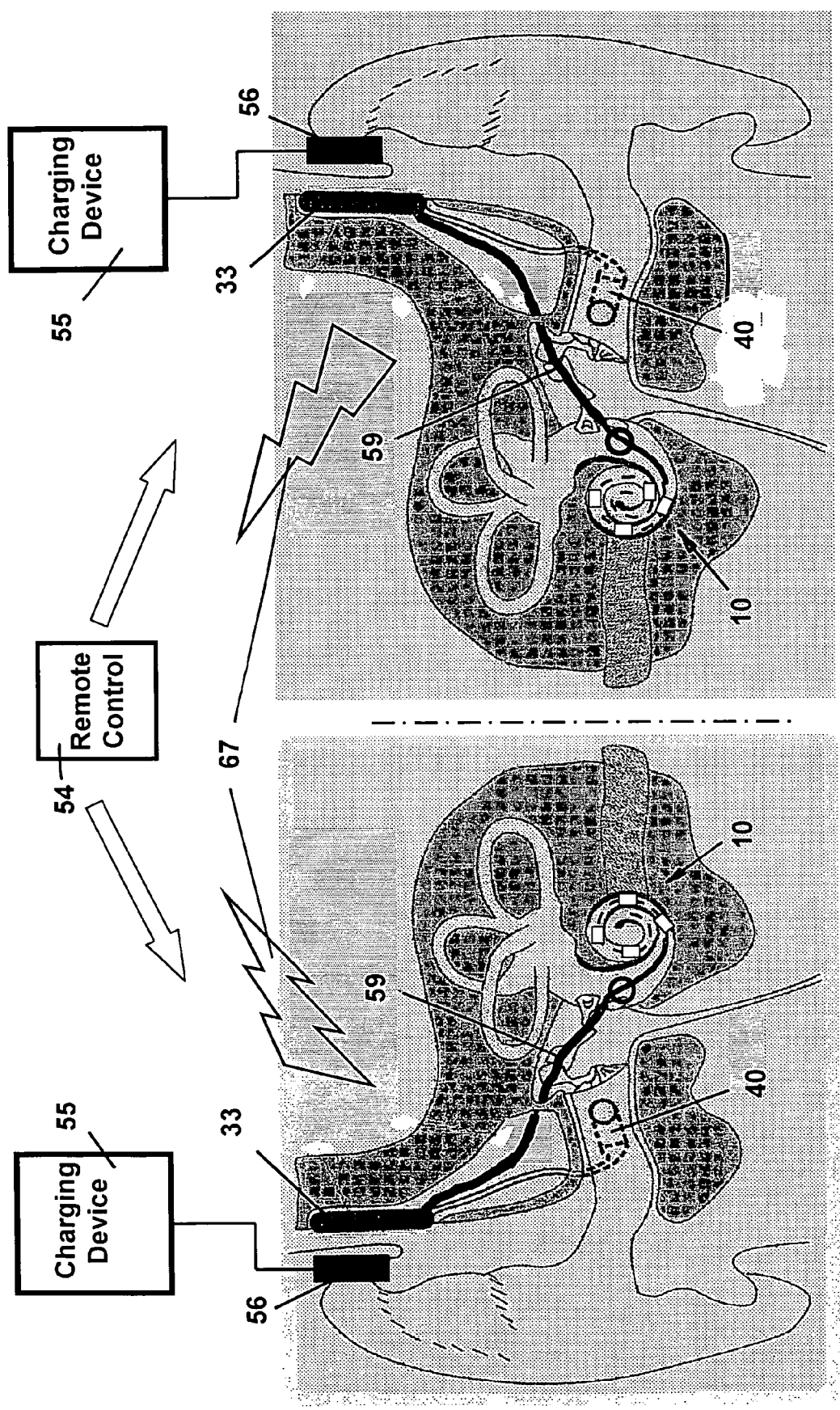
Figure 18:
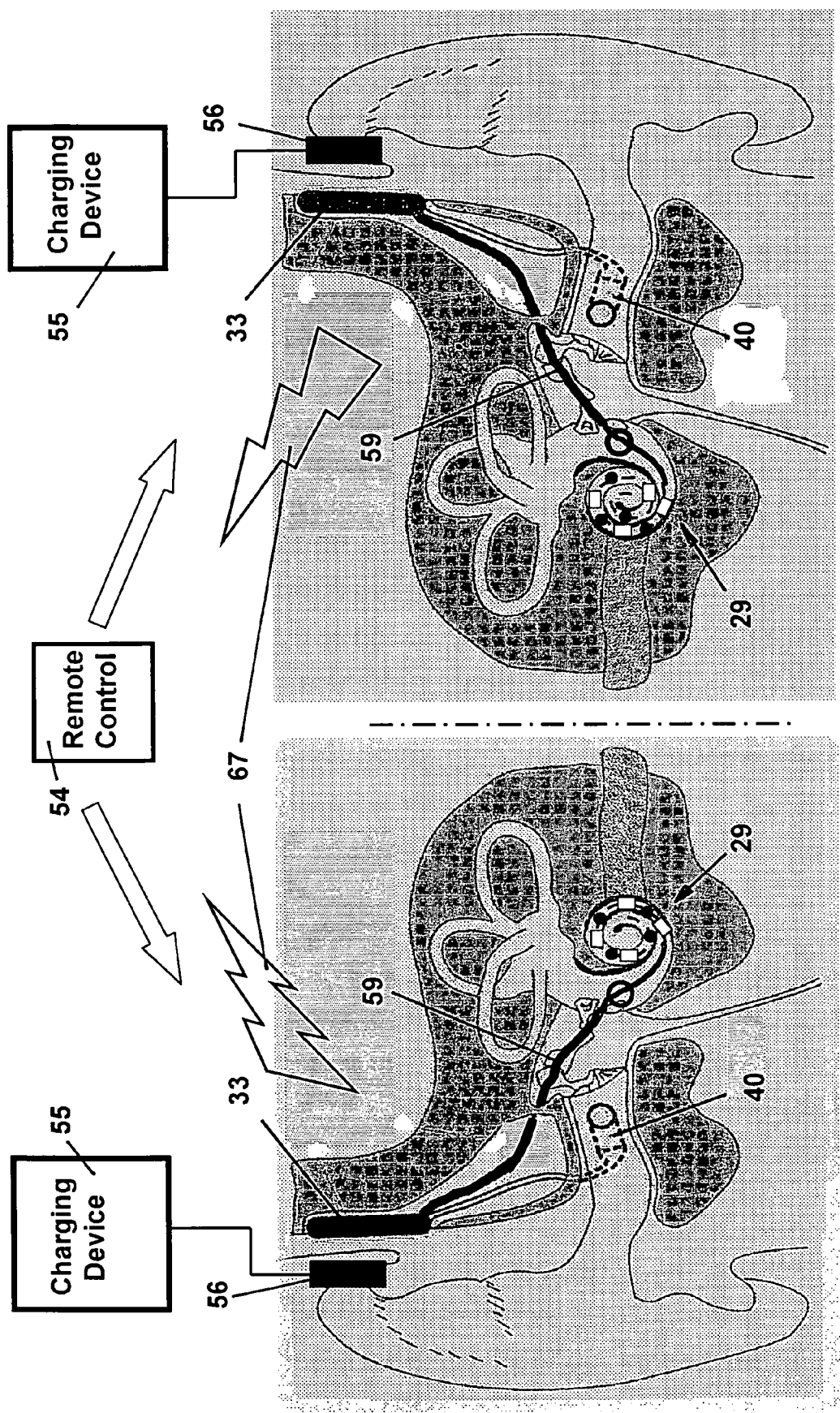
Figure 19:
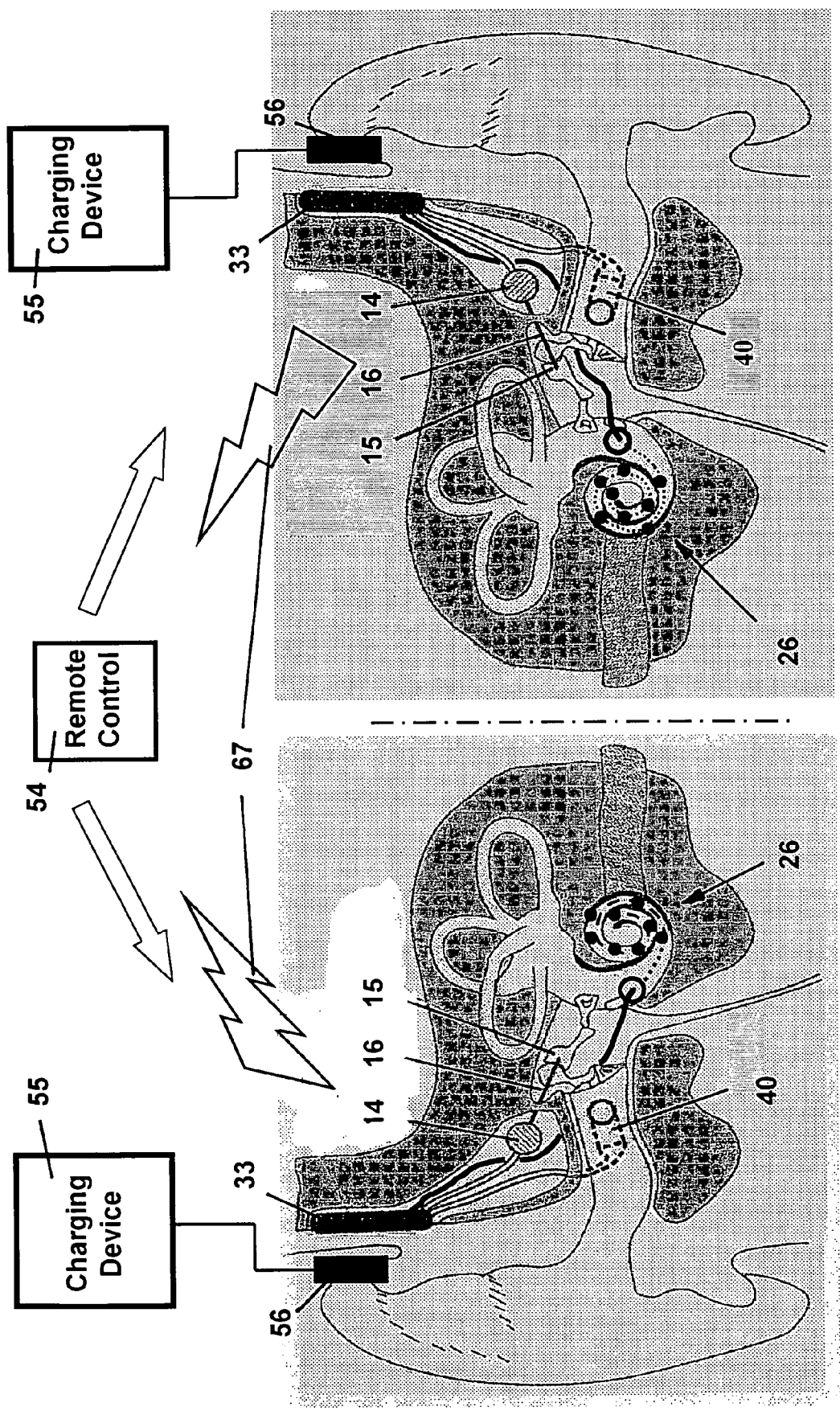
Figure 20:
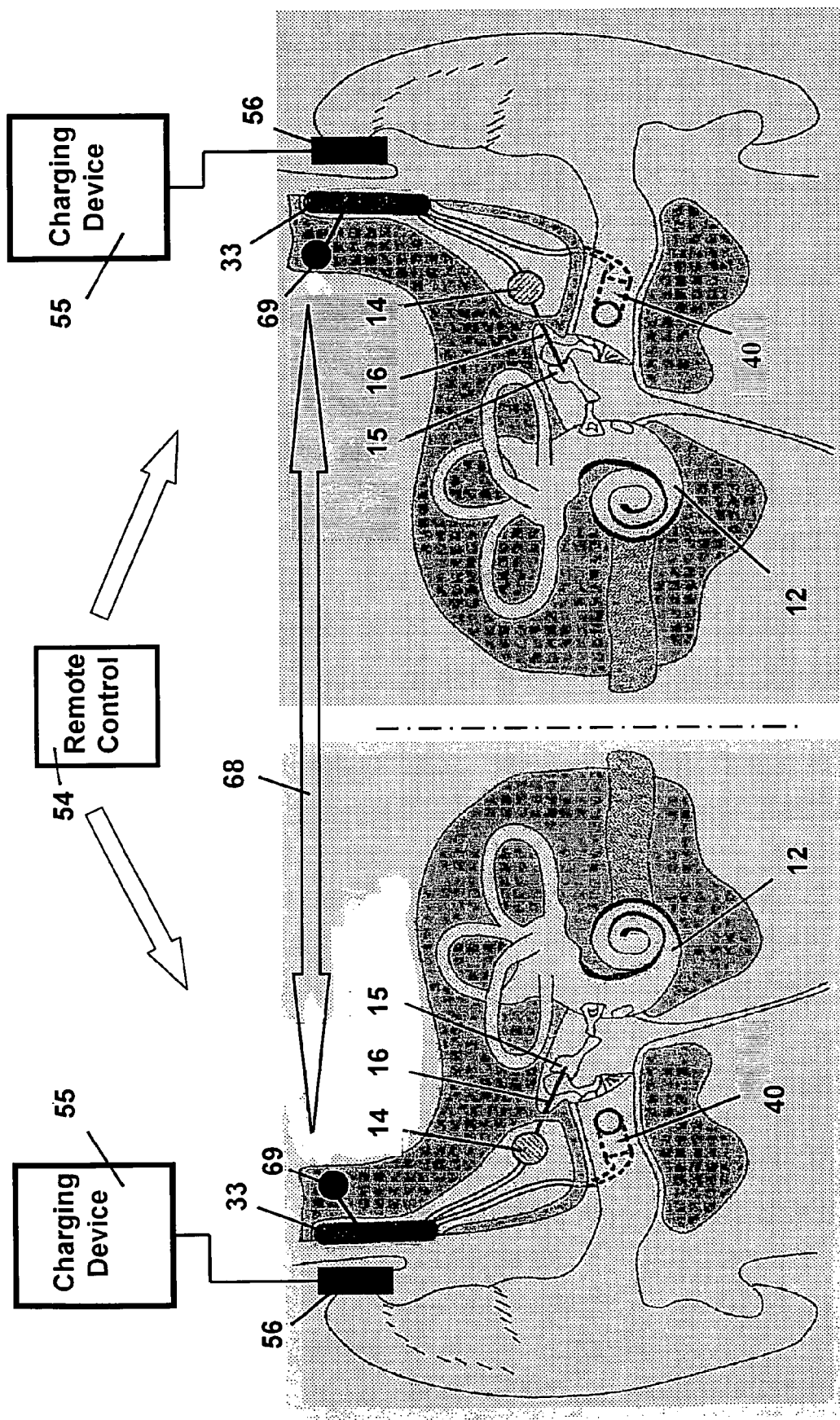
Figure 21:
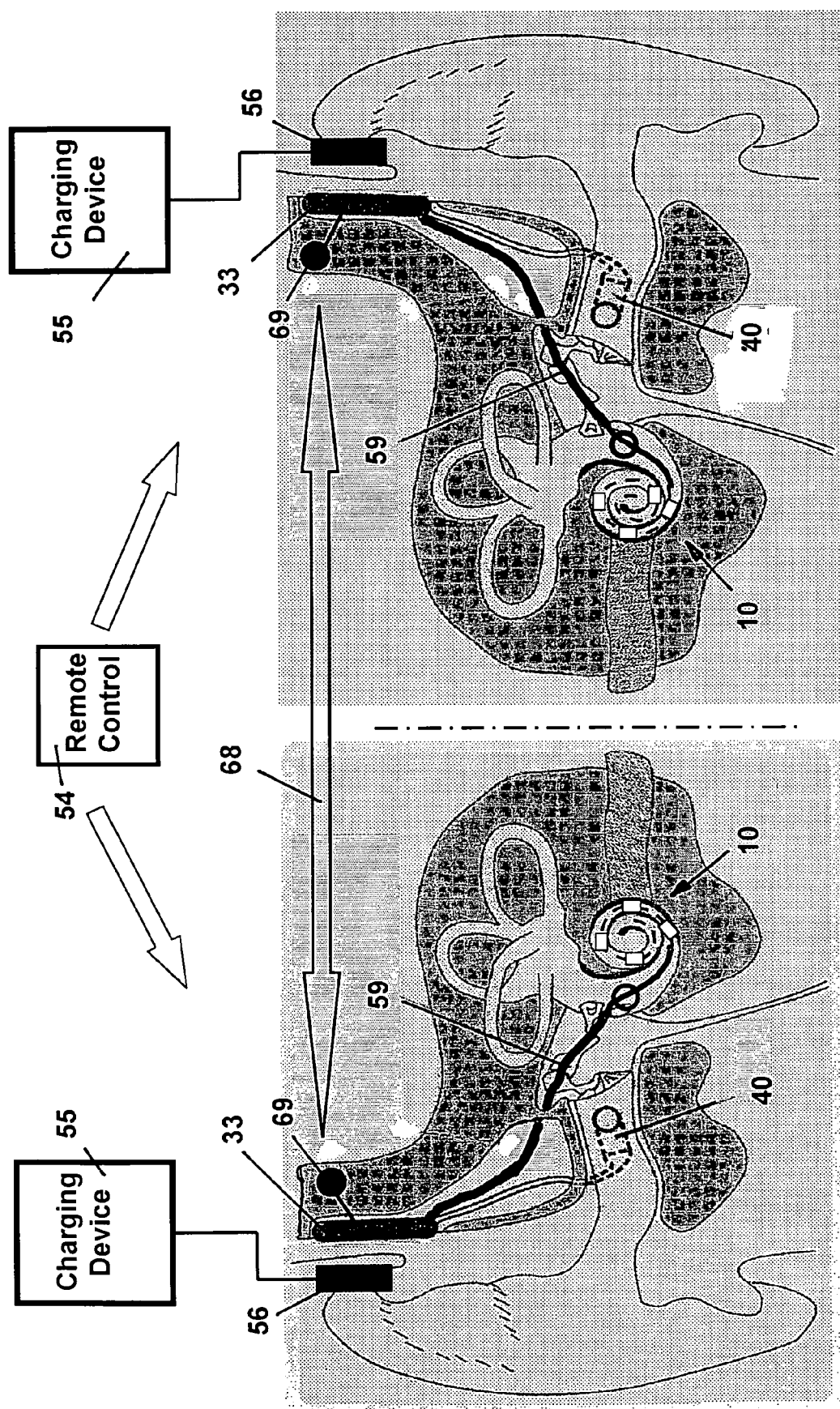
Figure 22:
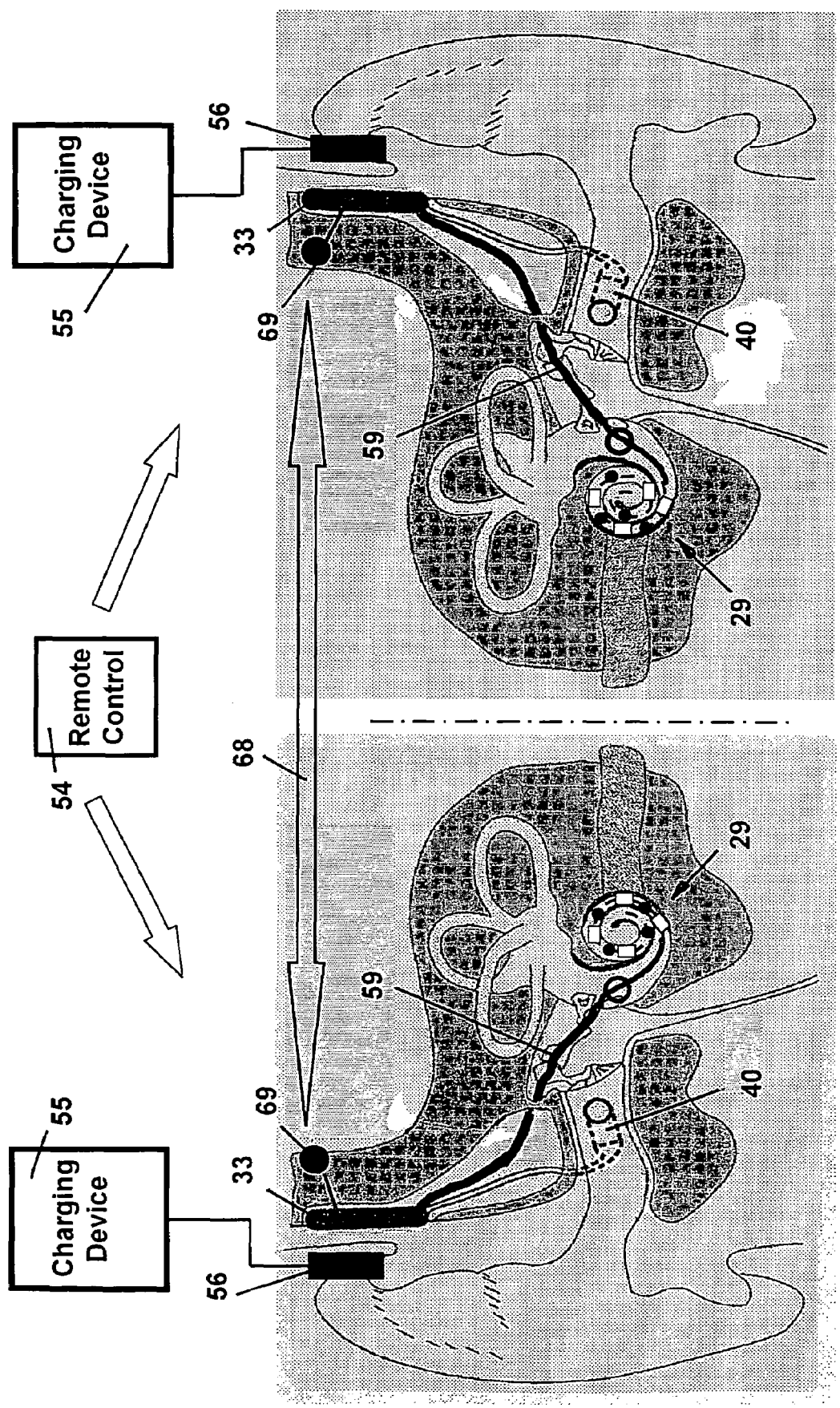
Figure 23:
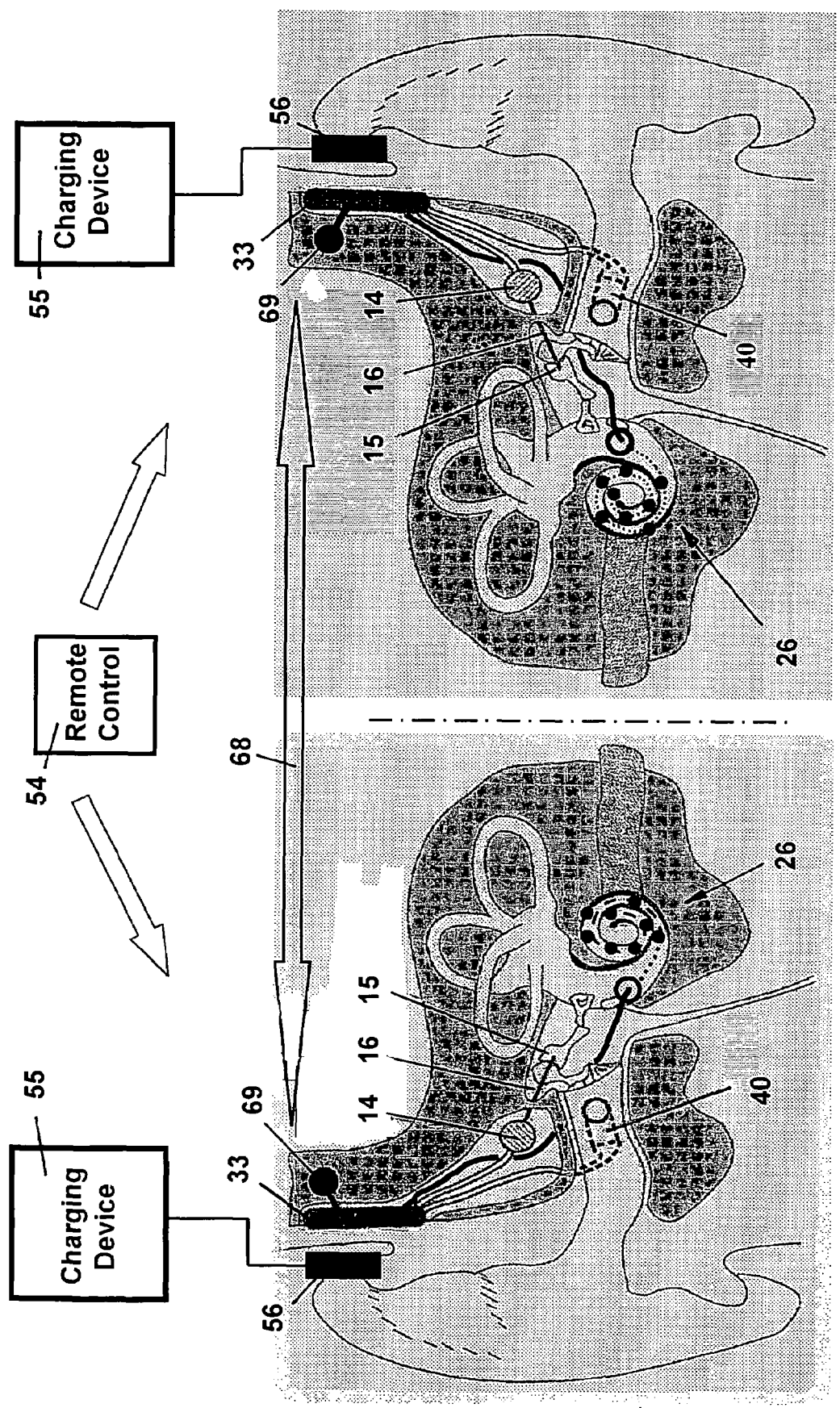
Figure 24:
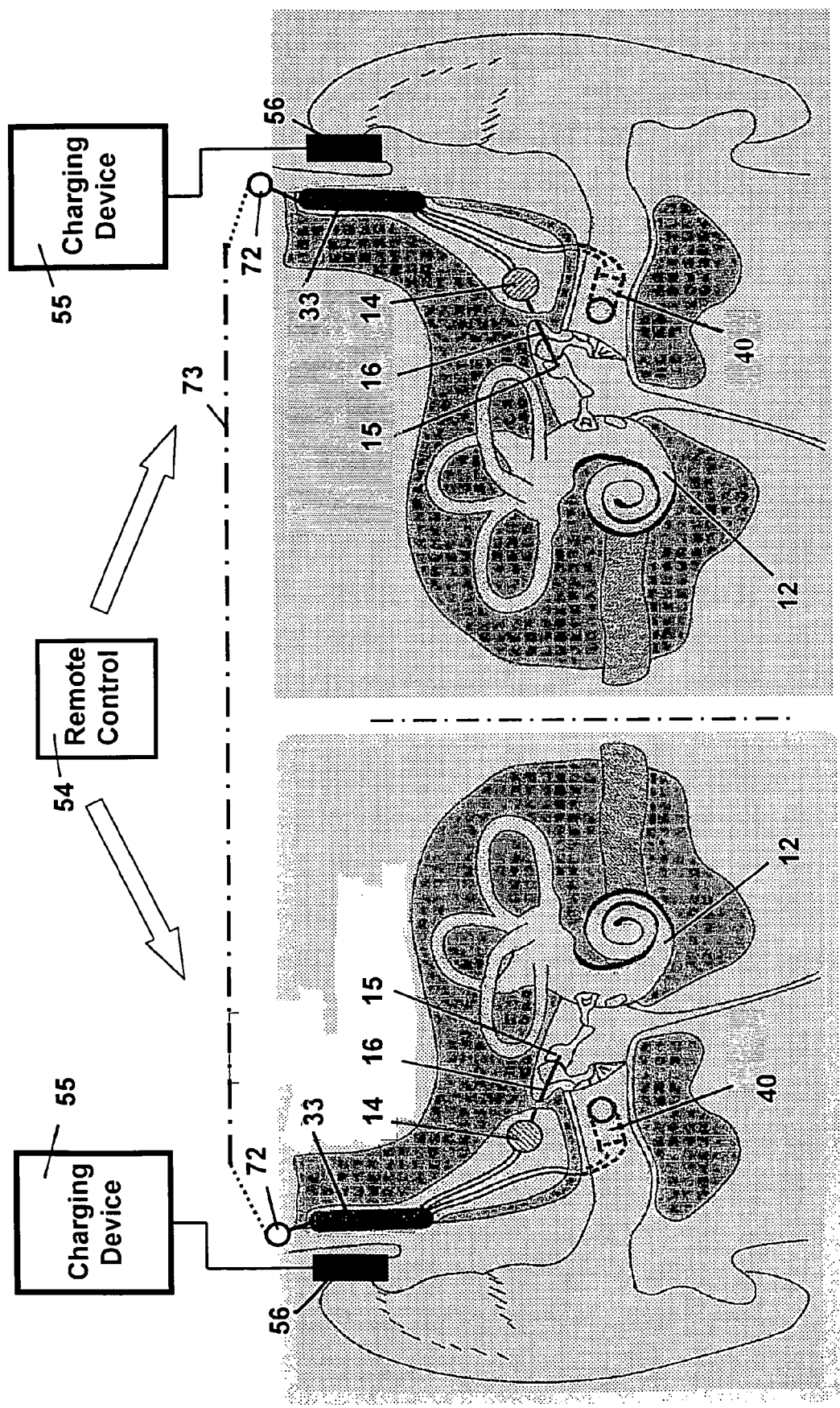
Figure 25:
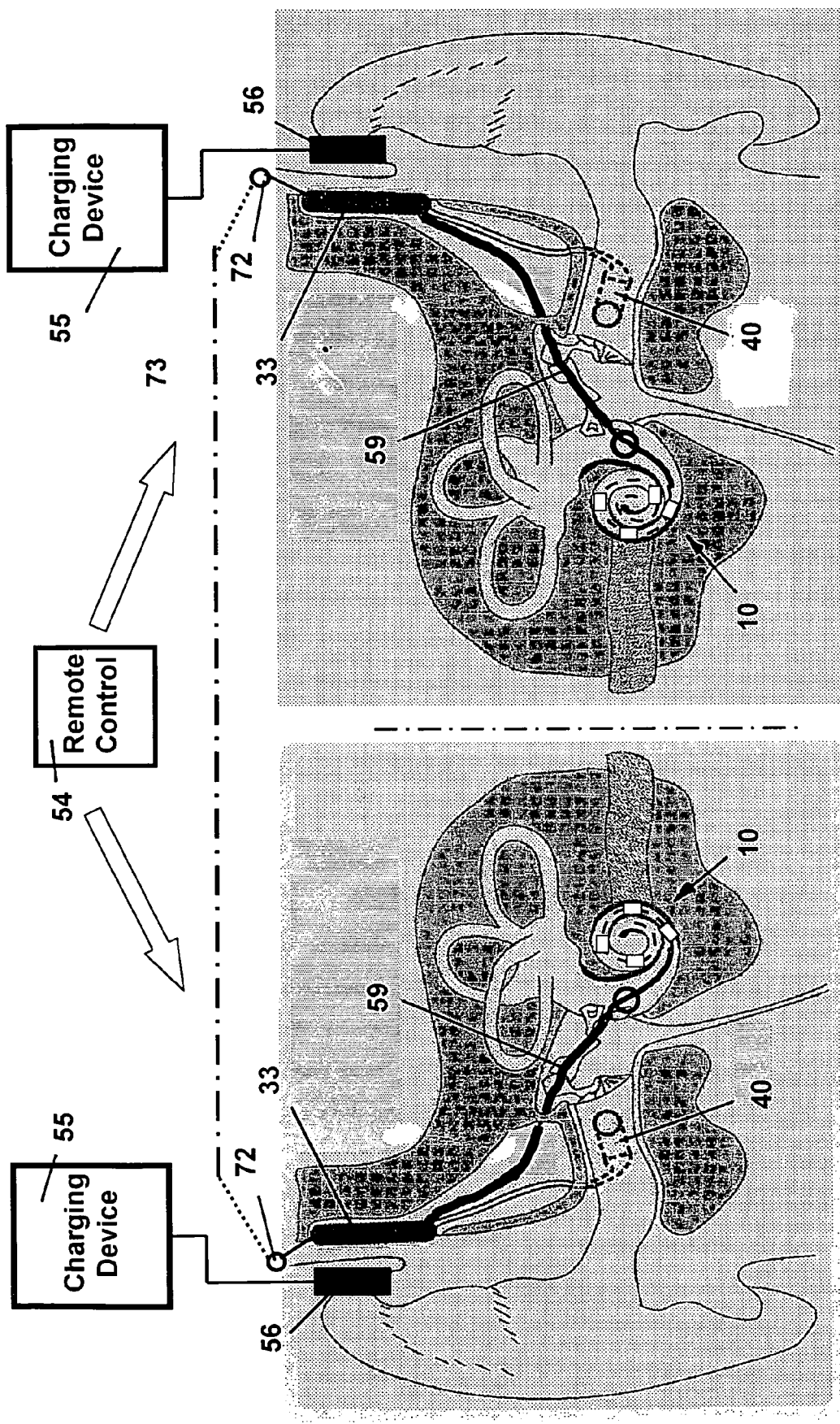
Figure 26:
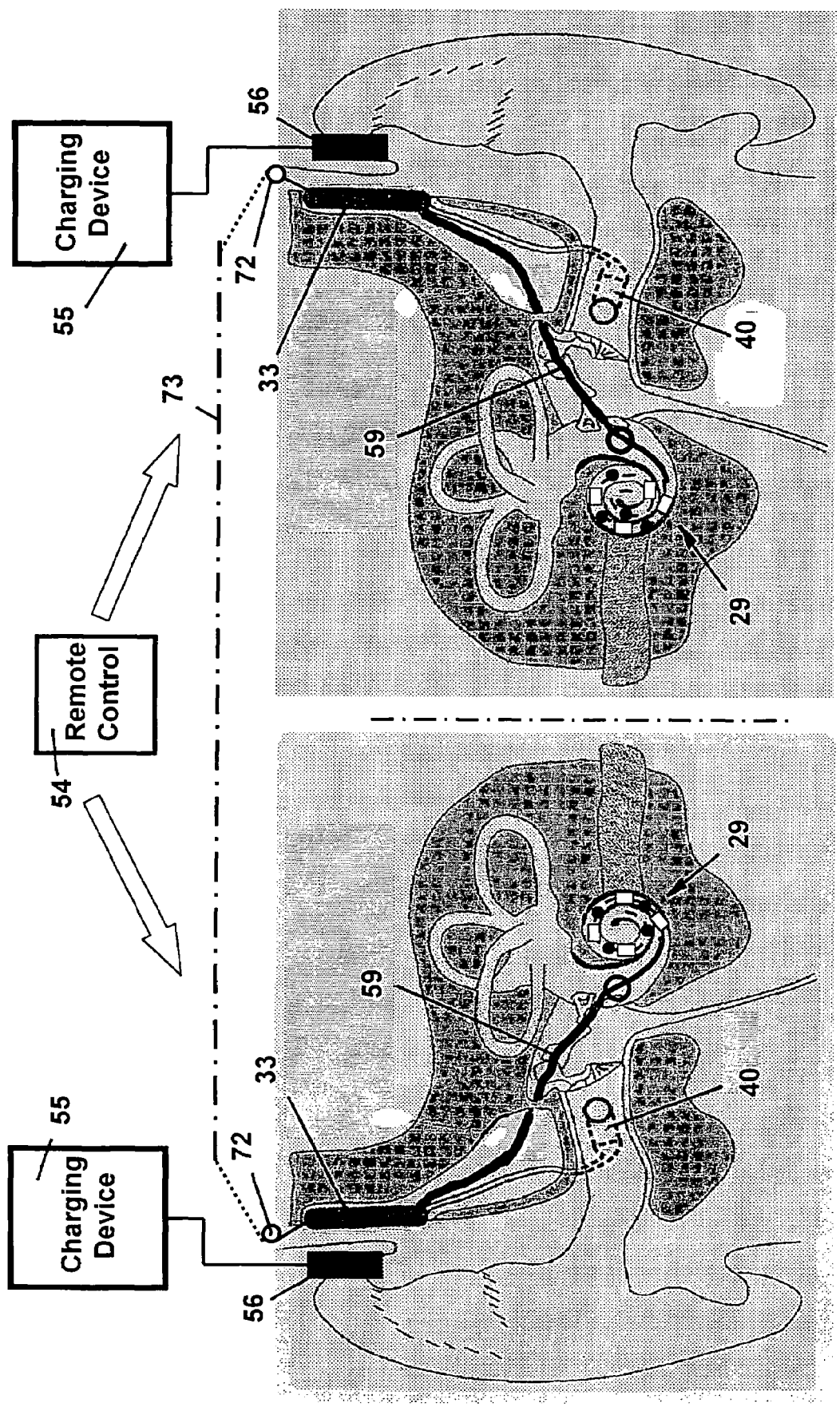
Figure 27:
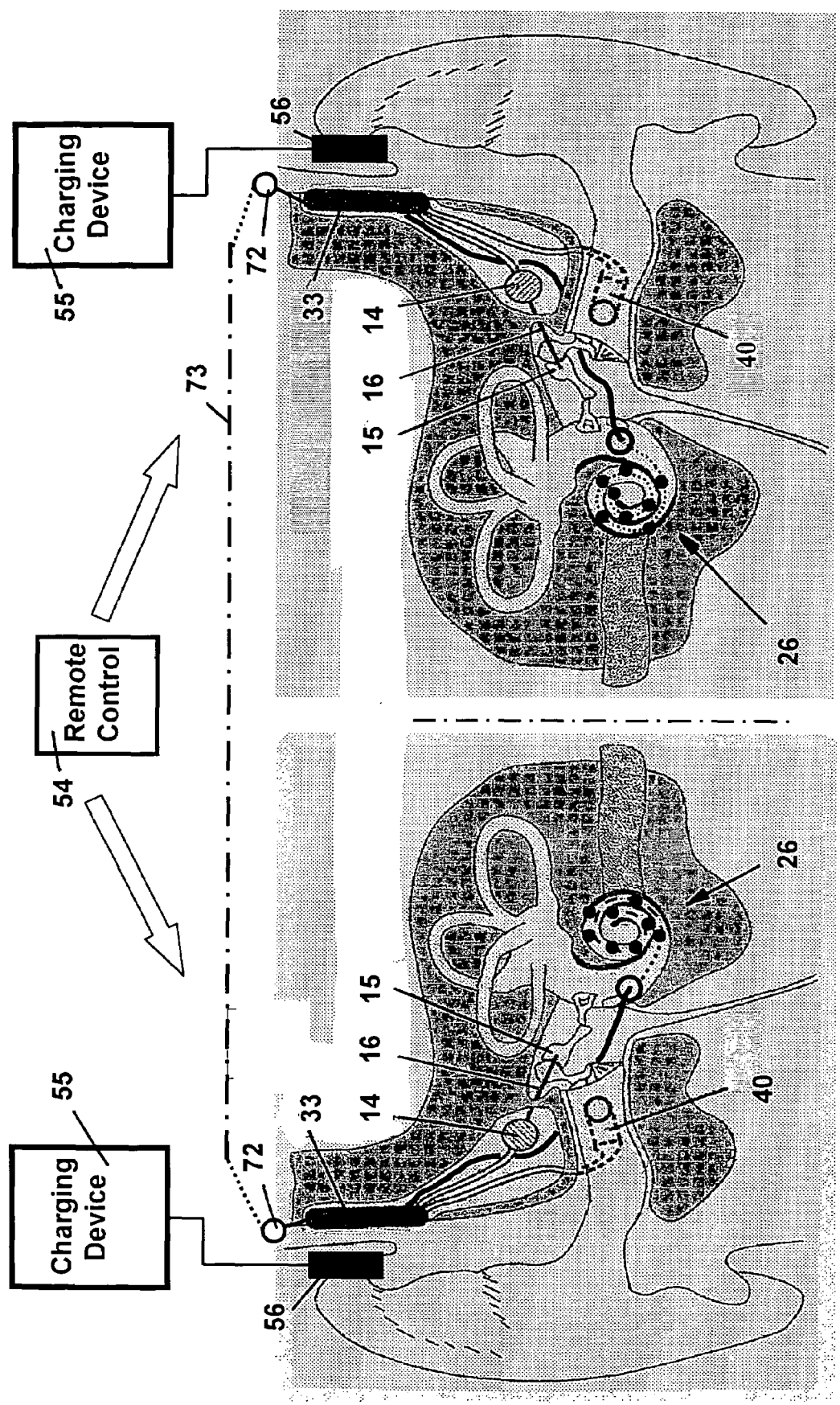

FIGS. 16, 17, 18 & 19 each show the binaural application of a hearing implant in which the signal processing units 34 in the electronic modules 33 on both sides of the skull communicate with one another via a wireless connection, for example a bidirectional high frequency section indicated at 67 such that optimum binaural sensor signal processing and actuator triggering in the two implanted inner ears are achieved. There are also transcutaneous charging devices 55, 56 for the case of implant-side secondary energy storage elements (batteries 52) and a wireless remote control 54 for use by the implant wearer which synchronously controls the two electronic modules 33. The embodiments of FIGS. 16 to 19 differ from one another only with respect to the actuator arrangements. The actuator arrangements as shown in FIGS. 16, 17, & 18 correspond to those of FIGS. 12, 13 & FIG. 14, respectively. The actuator arrangement shown in FIG. 19 corresponds to that as shown in FIG. 5.

The binaural execution of the hearing implants as shown in FIGS. 20, 21, 22, & 23 differ from that of FIGS. 16, 17, 18, & 19, respectively, only in that there is a solid borne sound-coupled ultrasonic section 68 with ultrasonic couplers 69 for wireless communication between the electronic modules 33 of the two system units. Here, for example, the digital, bidirectional information is preferably amplitude modulated or frequency modulated onto a carrier in the ultrasonic range. The ultrasonic couplers 69 can be, as shown in FIGS. 20 to 23, ultrasonic transmitters and receivers which are locally separated from the electronic module 33, which are connected via electrical lines, and which are preferably coupled securely in the mastoid area to the skull bone. The ultrasonic couplers however can also be integrated in the electronic modules 33 (not shown) when the electronic modules are implanted in the mastoid area such that ultrasonic solid borne transmission can take place through the skull bone.

Further modified embodiments of a binaurally formed hearing implant are shown in FIGS. 24, 25, 26, & 27. In these embodiments, in contrast to the embodiments of FIGS. 12 to 23, for example, the digital, bidirectional information is preferably amplitude modulated or frequency modulated on the implant side onto a carrier and applied to the implanted electrodes 72 which are part of a data transmission section 73 which leads through the body tissue of the implant wearer. Thus, a modulated tissue current is obtained which, in a known manner (U.S. Pat. No. 5,113,859), provides for the desired communication between the signal processing modules 34 of the two system units. The embodiments of FIGS. 24 to 27, in turn, differ from one another only with respect to the actuator arrangements. The latter correspond to the actuator arrangement as shown in FIGS. 20, 21, 22, & 23, respectively.

It goes without saying that a partially implantable system can also be binaurally applied and that then provisions can be made for communication between the two system units preferably according to the embodiments of binaural applications of fully implantable systems which are shown in FIGS. 12 to 27.

While various embodiments in accordance with the present invention have been shown and described, it is understood that the invention is not limited thereto. These embodiments may be changed, modified and further applied by those skilled in the art. Therefore, this invention is not limited to the details shown and described previously but also includes all such changes and modifications which are encompassed by the appended claims.

We claim:

1. A system for rehabilitation of a recipient's hearing, comprising:
    at least one acoustic sensor configured to convert a sensed acoustical signal into an electrical audio signal;
    a fully implantable signal processing unit configured to process said audio signal, comprising:
        an adaptive speech analysis and recognition module configured to detect and extract prosodic features from said audio signal, and
        an adaptive speech synthesis module configured to convert said audio signal into an artificial speech signal based on said extracted prosodic features;
        said speech analysis and recognition module and said speech synthesis module each being re-programmable while said signal processing unit is implantable; and
    an actuator arrangement configured to provide output stimulation to one or more hearing structures of the recipient based on said artificial speech signal, comprising a flexible carrier member configured to be implanted in the cochlea of the recipient, and an array of actuators mounted in said flexible carrier member configured to stimulate the cochlea.

2. The system of claim 1, wherein said adaptive speech analysis and recognition module and said adaptive speech synthesis module are re-programmable via wireless telemetry means.

3. The system of claim 1, wherein said signal processing unit is further configured to transmit said audio signal to said actuator arrangement without converting said audio signal into said artificial speech signal, and wherein said actuator arrangement is configured to provide output stimulation based on said transmitted audio signal.

4. The system of claim 3, wherein said adaptive speech analysis and recognition module and said adaptive speech synthesis module are configured to be turned off to enable processing of said audio signal without converting said audio signal to said artificial speech signal.

5. The system of claim 4, further configured to automatically turn off said adaptive speech analysis and recognition module and said adaptive speech synthesis module to permit processing of said audio signal without converting said audio signal into said artificial speech signal.

6. The system of claim 4, further configured to turn off said adaptive speech analysis and recognition module and said adaptive speech synthesis module to permit processing of said audio signal without converting said audio signal into said artificial speech signal in response to a control signal from a remote control.

7. The system of claim 1, wherein said adaptive speech analysis and recognition module is configured to assign said audio signal to phonetic or lexical categories, and wherein said adaptive speech synthesis module is configured to convert said audio signal assigned to phonetic or lexical categories to said artificial speech signal.

8. The system of claim 1, wherein said adaptive speech analysis and recognition module comprises:
    a digitally implemented neural network having automatic algorithms configured to detect and extract said prosodic features from said audio signal.

9. The system of claim 1, wherein said adaptive speech analysis and recognition module comprises:
    a digitally implemented neural network having automatic algorithms configured to assign said audio signal to phonetic or lexical categories.

10. The system of claim 1, wherein said adaptive speech synthesis module comprises:
    a digitally implemented neural network configured to convert said audio signal into said artificial speech signal based on said extracted prosodic features.

11. The system of claim 1, wherein said signal processing unit further comprises:
    modules configured to perform tinnitus masking.

12. The system of claim 11, wherein said modules configured to perform tinnitus masking are configured to perform said tinnitus masking simultaneously with said conversion of said audio signal into said artificial speech signal.

13. The system of claim 1, wherein said adaptive speech analysis and recognition module is further configured to analyze said audio signal by performing speech segmentation or recognition.

14. The system of claim 1, wherein said signal processing unit further comprises:
    adaptive signal processing algorithms configured to perform additional processing of said audio signal, and wherein said adaptive signal processing algorithms are reprogrammable after implantation of said signal processing unit.

15. The system of claim 1, wherein said system further comprises:
    a rewritable implantable storage arrangement for accommodating and reproducing operating programs, wherein the contents of said storage arrangement may be changed or replaced via wireless telemetry means.

16. The system of claim 1, wherein said speech analysis and recognition module and said speech synthesis module comprise:
    dynamic modules configured to optimize speech analysis and recognition and speech synthesis.

17. The system of claim 1, wherein said at least one acoustic sensor configured to convert a sensed acoustical signal into an electrical audio signal comprises:
    at least one subcutaneously implantable acoustic sensor.

18. The system of claim 1, wherein said actuator arrangement comprises:
    at least one extracochlear actuator configured to provide excitation to fluid-filled inner-ear spaces of the recipient.

19. The system of claim 18, wherein said extracochlear actuator comprises:

one or more of an acoustic stimulator or an electromechanical converter.

20. The system of claim 1, wherein said array of electromechanical converters further comprise:
mechanical actuation elements embedded in said carrier member between said converters configured to minimize mechanical wave propagation from a converter within said carrier member to adjacent converters.

21. The system of claim 1, wherein said array of actuators comprises:
an array of stimulating electrodes.

22. The system of claim 1, wherein said array of actuators comprises:
a combination of electromechanical converters and stimulating electrodes.

23. A system for rehabilitating a recipient's hearing, comprising:
at least one acoustic sensor configured to convert a sensed acoustical signal into an electrical audio signal;
a signal processing unit configured to process said audio signal, comprising:
a speech analysis and recognition module configured to detect and extract prosodic features from said audio signal, and
a speech synthesis module configured to convert said audio signal into an artificial speech signal based on said extracted prosodic features;
an actuator arrangement configured to provide output stimulation to one or more hearing structures of the recipient based on said artificial speech signal, comprising a flexible carrier member configured to be implanted in the cochlea of the recipient, and an array of actuators mounted in said flexible carrier member configured to stimulate the cochlea; and
wherein said signal processing unit is further configured to select processing of said audio signal without converting said audio signal into said artificial speech signal, and wherein said actuator arrangement is configured to provide output stimulation based on said processed audio signal.

24. The system of claim 23, wherein said speech analysis and recognition module and said speech synthesis module are configured to be turned off to enable processing of said audio signal without converting said audio signal to said artificial speech signal.

25. The system of claim 24, wherein said signal processing unit is configured to automatically turn off said speech analysis and recognition module and said speech synthesis module to permit processing of said audio signal without converting said audio signal into said artificial speech signal.

26. The system of claim 24, wherein said signal processing unit is configured to turn off said speech analysis and recognition module and said speech synthesis module to permit processing of said audio signal without converting said audio signal into said artificial speech signal in response to a control signal from a remote control.

27. The system of claim 23, wherein said speech analysis and recognition module and said speech synthesis module are re-programmable.

28. The system of claim 23, wherein said speech analysis and recognition module is configured to assign said audio signal to phonetic or lexical categories, and wherein said speech synthesis module is configured to convert said audio signal assigned to phonetic or lexical categories to said artificial speech signal.

29. The system of claim 23, wherein said speech analysis and recognition module comprises:
a digitally implemented neural network having automatic algorithms configured to detect and extract said prosodic features from said audio signal.

30. The system of claim 23, wherein said speech analysis and recognition module comprises:
a digitally implemented neural network configured to assign said audio signal to phonetic or lexical categories with automatic algorithms.

31. The system of claim 23, wherein said speech synthesis module comprises:
a digitally implemented neural network configured to convert said audio signal into said artificial speech signal based on said extracted prosodic features.

32. The system of claim 23, wherein said signal processing unit further comprises:
modules configured to perform tinnitus masking.

33. The system of claim 32, wherein said modules configured to perform tinnitus masking are configured to perform said tinnitus masking simultaneously with said conversion of said audio signal into said artificial speech signal.

34. The system of claim 23, wherein said speech analysis and recognition module is further configured to analyze said audio signal by performing speech segmentation or recognition.

35. The system of claim 23, wherein said signal processing unit further comprises:
adaptive signal processing algorithms configured to perform additional processing of said audio signal, and wherein said adaptive signal processing algorithms are reprogrammable after implantation of said signal processing unit.

36. The system of claim 23, wherein said system further comprises:
a rewritable implantable storage arrangement for accommodating and reproducing operating programs, wherein the contents of said storage arrangement may be changed or replaced via wireless telemetry means.

37. The system of claim 23, wherein said speech analysis and recognition module and said speech synthesis module comprise:
dynamic modules configured to optimize speech analysis and recognition and speech synthesis.

38. The system of claim 23, wherein said at least one acoustic sensor configured to convert a sensed acoustical signal into an electrical audio signal comprises:
at least one subcutaneously implantable acoustic sensor.

39. The system of claim 23, wherein said actuator arrangement comprises:
at least one extracochlear actuator configured to provide excitation to fluid-filled inner-ear spaces of the recipient.

40. The system of claim 39, wherein said extracochlear actuator comprises:
one or more of an acoustic stimulator or an electromechanical converter.

41. The system of claim 23, wherein said array of electromechanical converters further comprise:
mechanical actuation elements embedded in said carrier member between said converters configured to minimize mechanical wave propagation from a converter within said carrier member to adjacent converters.

42. The system of claim 23, wherein said array of actuators comprises:
an array of stimulating electrodes.

43. The system of claim 23, wherein said array of actuators comprises:

a combination of electromechanical converters and stimulating electrodes.

44. A method for processing a sound in a fully implantable cochlear implant, comprising:
converting a sensed acoustical signal into an electrical audio signal; processing said audio signal comprising:
detecting an extracting prosodic features from said audio signal with a first dynamic module; and
converting said audio signal into an artificial speech signal based on said extracted prosodic features at a second dynamic module;
stimulating one or more hearing structures of a recipient based on said artificial speech signal with an actuator arrangement comprising a flexible carrier member configured to be implanted in the cochlea of the recipient, and an array of actuators mounted in said flexible carrier member configured to stimulate the cochlea; and
allowing said first and second dynamic modules to optimize said processing.

45. The method of claim 44, further comprising:
reprogramming said first and second modules via wireless telemetry means.

46. The method of claim 44, further comprising:
processing said audio signal without converting said audio signal into said artificial speech signal, and
stimulating the one or more hearing structures of the recipient based on said non-converted audio signal.

47. The method of claim 46, further comprising:
turning off said first and second dynamic modules to enable processing of said audio signal without converting said audio signal to said artificial speech signal.

48. The method of claim 46, further comprising:
allowing said first and second dynamic modules to automatically turn off to permit processing of said audio signal without converting said audio signal into said artificial speech signal.

49. The system of claim 44, further comprising:
performing additional processing of said audio signal with adaptive signal processing algorithms.

* * * * *

UNITED STATES PATENT AND TRADEMARK OFFICE
CERTIFICATE OF CORRECTION

| | | |
|---|---|---|
| PATENT NO. | : 7,376,563 B2 | Page 1 of 1 |
| APPLICATION NO. | : 09/896836 | |
| DATED | : May 20, 2008 | |
| INVENTOR(S) | : Hans Leysieffer et al. | |

It is certified that error appears in the above-identified patent and that said Letters Patent is hereby corrected as shown below:

On the title page Item (30):

Foreign Priority Documents should be listed as follows:

<u>DE 100 31 832.0 June 30, 2000</u>

Column 5, line 39 reads "stimuli do not fundamentally correspond to thee biologically", it should read -- stimuli do not fundamentally correspond to the biologically --.

In the Claims:

Col. 31, claim 44, line 7 reads "detecting an extracting prosodic features from said", it should read -- detecting and extracting prosodic features from said --.

Signed and Sealed this

Eleventh Day of November, 2008

JON W. DUDAS
*Director of the United States Patent and Trademark Office*